United States Patent [19]
Suto et al.

[11] Patent Number: 5,935,966
[45] Date of Patent: *Aug. 10, 1999

[54] PYRIMIDINE CARBOXYLATES AND RELATED COMPOUNDS AND METHODS FOR TREATING INFLAMMATORY CONDITIONS

[75] Inventors: Mark J. Suto, La Jolla; Leah M. Gayo, San Diego; Moorthy S. S. Palanki, Encinitas; Lynn J. Ransone-Fong, San Diego, all of Calif.

[73] Assignee: Signal Pharmaceuticals, Inc., San Diego, Calif.

[ * ] Notice: This patent is subject to a terminal disclaimer.

[21] Appl. No.: 08/807,677

[22] Filed: Feb. 27, 1997

Related U.S. Application Data

[63] Continuation-in-part of application No. 08/574,406, Dec. 18, 1995

[60] Provisional application No. 60/003,109, Sep. 1, 1995.

[30] Foreign Application Priority Data

Aug. 30, 1996 [WO] WIPO .................. PCT/US96/14089

[51] Int. Cl.⁶ .................. C07D 239/02; A01N 43/54
[52] U.S. Cl. .................. 514/275; 544/331; 544/332
[58] Field of Search .................. 544/332, 331; 514/275

[56] References Cited

U.S. PATENT DOCUMENTS

| | | | |
|---|---|---|---|
| 3,670,077 | 6/1972 | Freeman et al. | 424/200 |
| 3,814,762 | 6/1974 | Santilli et al. | 260/256.5 R |
| 5,703,106 | 12/1997 | Früh et al. | 514/378 |

FOREIGN PATENT DOCUMENTS

| | | |
|---|---|---|
| 1572620 | 6/1969 | France . |
| WO 97/09325 | 3/1997 | WIPO . |

OTHER PUBLICATIONS

Assy et al., "Some reactions with ethyl 4–(mercapto/chloro)–6–methyl–2–phenylpyrimidine–5–carboxylate," Chemical Abstracts 125(5): p. 1148, Abstract No. 58437p, 1996.

Primary Examiner—Richard L. Raymond
Assistant Examiner—Tamthom N. Truong
Attorney, Agent, or Firm—Seed and Berry LLP

[57] ABSTRACT

Compounds having utility as anti-inflammatory agents in general and, more specifically, for the prevention and/or treatment of immunoinflammatory and autoimmune diseases are disclosed. The compounds are pyrimidine-containing compounds and, in one embodiment, are esters of the same. Methods are also disclosed for preventing and/or treating inflammatory conditions by administering to an animal in need thereof an effective amount of a compound of this invention, preferably in the form of a pharmaceutical composition.

24 Claims, 5 Drawing Sheets

PYRIMIDINE CARBOXYLATES AND RELATED COMPOUNDS AND METHODS FOR TREATING INFLAMMATORY CONDITIONS

CROSS-REFERENCE TO RELATED APPLICATIONS

This application claims priority from PCT/US96/14089 filed Aug. 30, 1996 and U.S. Provisional Application No. 60/003,109 filed Sep. 1, 1995, and is a continutation-in-part of U.S. application No. 08/574,406 filed Dec. 18, 1995.

TECHNICAL FIELD

The present invention relates generally to compounds that block intracellular signal transduction and activation of transcription factors, and to methods for preventing or treating immunoinflammatory and autoimmune diseases.

BACKGROUND OF THE INVENTION

Signals necessary for cell growth, differentiation, response to bioregulatory molecules, infectious agents and physiological stress involve changes in the rates of gene expression. The ability to respond appropriately to such signaling events challenge the survival of the cell and ultimately the organism. Perturbations in the normal regulation of these specific genetic responses can result in pathogenic events which lead to acute and chronic disease.

In certain autoimmune diseases or chronic inflammatory states, continuous activation of T-cells eventually leads to a self-perpetuating destruction of normal tissues or organs. This is caused by the induction of adhesion molecules, chemotaxis of leukocytes, activation of leukocytes and the production of mediators of inflammation. All of these events are regulated at the level of transcription for the production of new proteins, including cytokines. The production of cytokines, as well as a number of other cellular regulators, is controlled by a family of proteins known as transcription factors (TFs). These transcription factors, when activated, bind to specific regions on the DNA and act as molecular switches or messengers to induce or upregulate gene expression. The activation of these TFs is caused by a variety of external signals including physiological stress, infectious agents and other bioregulatory molecules. Once the plasma membrane receptors are activated, a cascade of protein kinases and second messengers are induced which, in turn, result in the production of RNA transcripts. The end result is the production of proinflammatory proteins via translation and processing of the RNA transcripts.

This activation system can, at times, be very robust. For example, a specific set of external signals could result in a single transcription factor to induce many proteins responsible for a given disease. Therefore, regulating this process by disrupting the production of activated TF(s) has the potential to attenuate the production of the associated pathological proteins, thereby halting or reversing the course of the disease.

Two transcription factors, NFκB and AP-1, have been shown to regulate the production of many proinflammatory cytokines and related proteins that are elevated in immunoinflammatory diseases. These TFs regulate interleukin-1 (IL-1), interleukin-2 (IL-2), tumor necrosis factor-α (TNFα), interleukin-6 (IL-6) and interleukin-8 (IL-8) levels in a variety of cell types. For example, NFκB and other related complexes are involved in the rapid induction of genes whose products function in protective and proliferative responses upon exposure of cells to external stimuli. Similarly, AP-1 has a significant role in the regulation of interleukin-2 (IL-2) and tumor necrosis factor-α (TNF-α) transcription during T-cell activation. In addition, TNF-α and IL-1 are strong activators of collagenase, gelatinase and stromelysin gene expression, which require a single AP-1 binding site in the promoter region of these genes. Therefore, an inhibitor of NFκB and/or AP-1 activation would coordinately repress the activities of a series of proteinases. In addition, cell adhesion molecules are also controlled by these TFs. All of these proteins have been shown to play a role in diseases, including osteoarthritis, transplant rejection, ischemia, reperfusion injury, trauma, certain cancers and viral disorders, and autoimmune diseases such as rheumatoid arthritis, multiple sclerosis, psoriasis, inflammatory bowel disease, glomerulonephritis, lupus and juvenile diabetes. In summary, the role of these TFs is to act as a transducer for certain stimuli that lead to immune, inflammatory, and acute phase responses.

Since many diseases are caused by the inappropriate production of proteins, conventional therapeutic approaches have focused on inhibiting function or activity of individual effector proteins. These treatments have not always proved to be effective and, at times, are associated with many undesirable side effects. Therefore, there is a need for new therapies for the prevention and/or treatment of immunoinflammatory and autoimmune diseases. More specifically, there is a need for compounds that prevent, preferably by inhibiting transcription at an early stage, the production of proteins associated with immunoinflammatory and autoimmune diseases. Furthermore, these compounds should inhibit the kinase(s) that regulate the activation of TFs such as NFκB and AP-1. The present invention fulfills these needs and provides further related advantages.

SUMMARY OF THE INVENTION

In brief, this invention is directed to compounds that block the activation of transcription factors (TFs), particularly NFκB and AP-1, and are believed to function through inhibition of a family of specific kinases. This results in a decrease in a number of proinflammatory proteins, including IL-1, IL-2, IL-8 and/or TNFα, which are responsible for tissue and organ damage associated with diseases such as rheumatoid arthritis, osteoarthritis, related autoimmune disorders and tissue rejection. Accordingly, compounds of the present invention are useful in, for example, the prevention of organ and tissue rejection associated with transplantation. Furthermore, the compounds of this invention also have utility in the prevention and/or treatment of immunoinflammatory and autoimmune diseases, as well as having general activity as anti-inflammatory agents.

In one embodiment of this invention, compounds are disclosed having the following general structure (I):

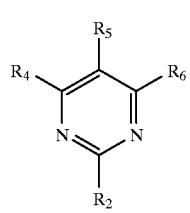

(I)

wherein $R_2$, $R_4$, $R_5$ and $R_6$ are as defined in the following detailed description.

3

In another embodiment, a pharmaceutical composition is disclosed containing one or more compounds of this invention in combination with a pharmaceutically or prophylactically acceptable carrier or diluent.

In a further embodiment, methods are disclosed for preventing and/or treating inflammatory conditions by administering to a warm-blooded animal in need thereof an effective amount of a compound of this invention. Such inflammatory conditions include both immunoinflammatory conditions and autoimmune diseases. In the practice of the disclosed methods, the compounds are preferably administered to the warm-blooded animal in the form or a pharmaceutical composition.

These and other aspects of this invention will become evident upon reference to the attached figures and the following detailed description.

DETAILED DESCRIPTION OF THE INVENTION

Figure 1:
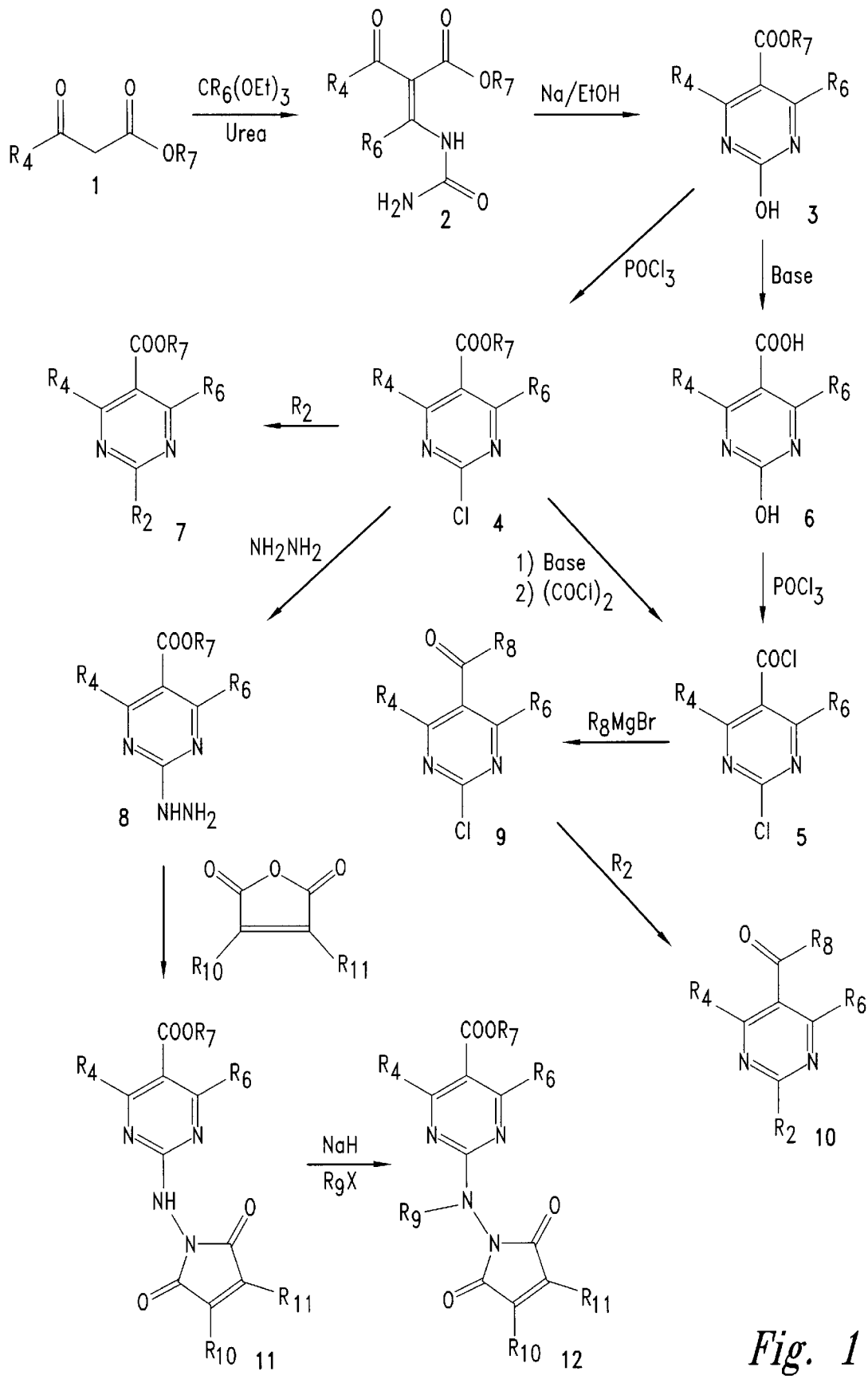
FIGS. 1, 2 and 3 illustrate reaction schemes for the synthesis of representative compounds of this invention.

As mentioned above, the compounds of this invention block activation of transcription factors (TFs), and thus have utility as anti-inflammatory agents in general, and in the prevention and/or treatment of a variety of conditions, including (but not limited to) immunoinflammatory and autoimnmune diseases. The compounds are believed to function by inhibiting, at an early stage, transcription of deleterious proteins associated with such conditions or diseases. It is believed that this is achieved by inhibiting the kinase(s) that regulate the activation of TFs, such as NFκB and/or AP-1. By disrupting the production of these activated TFs, synthesis of pathological proteins, including proinflammatory cytokines, associated with a series of immunoinflammatory and autoimmune diseases are effectively blocked at a transcriptional level. Accordingly, the compounds of this invention have activity in both the prevention and treatment of immunoinflammatory diseases such as rheumatoid arthritis, osteoarthritis and transplant rejection (tissue and organ), as well as autoimmune diseases such as multiple sclerosis.

The compounds of this invention are generally represented by the following structure (I):

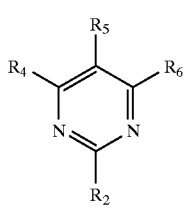

(I)

wherein $R_2$, $R_4$, $R_5$ and $R_6$ are as defined below.

In structure (I) above, $R_5$ is selected from the following chemical moieties (i), (ii), (iii) and (iv):

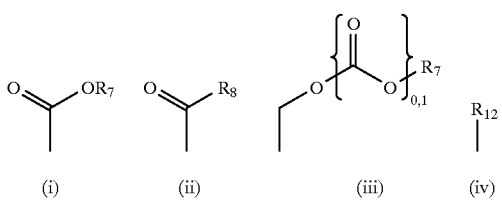

(i)   (ii)   (iii)   (iv)

wherein $R_7$ is selected from hydrogen and an unsubstituted or substituted $C_{1-8}$alkyl, $C_{6-12}$aryl or $C_{7-12}$aralkyl; $R_8$ is an unsubstituted or substituted $C_{1-8}$alkyl, $C_{6-12}$aryl or $C_{7-12}$aralkyl; and $R_{12}$ is selected from cyano and the following moieties:

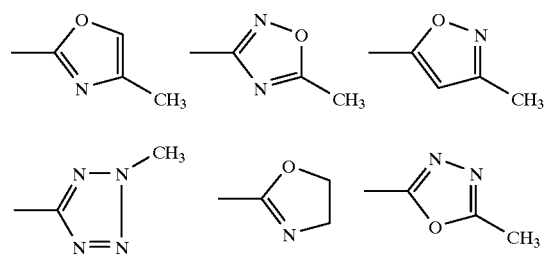

In a preferred embodiment, $R_7$ is a $C_{1-8}$ alkyl, and in a more preferred embodiment is selected from methyl and ethyl. Further, in a preferred embodiment, $R_8$ is selected from methyl and phenyl.

As used herein, the above terms have the following meaning:

A "$C_{1-8}$alkyl" is a straight chain or branched, cyclic or non-cyclic, saturated or unsaturated carbon chain containing from 1 to 8 carbon atoms. In one embodiment, the $C_{1-8}$alkyl is a fully saturated, straight chain alkyl selected from methyl, ethyl, n-propyl, n-butyl, n-pentyl and n-hexyl. In another embodiment, the $C_{1-8}$alkyl is a fully saturated cyclic alkyl selected from (but not limited to) cyclopropyl, cyclobutyl, cyclopentyl, cyclohexyl, methylenecyclopropyl and methylenecyclohexyl. In still a further embodiment, the $C_{1-8}$alkyl is a fully saturated, branched alkyl selected from (but not limited to) isopropyl, sec-butyl, isobutyl, tert-butyl, isopentyl and isohexyl. In yet a further embodiment, the $C_{1-8}$alkyl is an unsaturated straight chain alkyl selected from (but not limited to) ethylenyl, propylenyl, 1-butenyl, 1-pentenyl and 1-hexenyl.

A "$C_{6-12}$aryl" is an aromatic moiety containing from 6 to 12 carbon atoms. In one embodiment, the $C_{6-12}$aryl is selected from (but not limited to) phenyl, tetralinyl, and napthalenyl. In a preferred embodiment, the $C_{6-12}$aryl is phenyl.

A "$C_{7-12}$aralkyl" is an arene containing from 7 to 12 carbon atoms, and has both aliphatic and aromatic units. In one embodiment, the $C_{7-12}$aralkyl is selected from (but not limited to) benzyl, ethylbenzyl, propylbenzyl and isobutylbenzyl.

A "substituted" $C_{1-8}$alkyl, $C_{6-12}$aryl or $C_{7-12}$aralkyl is a $C_{1-8}$alkyl, $C_{6-12}$aryl or $C_{7-12}$aralkyl having one or more hydrogens replaced with a substituent selected from halogen (including —F, —Cl, —Br and —I), —OH, —R, —OR, —COOH, —COOR, —COR, —CONH$_2$, —NH$_2$, —NHR, —NRR, —NO$_2$, —SH, —SR, —SOOR, —SO$_3$R and —SOR, where each occurrence of R is independently selected from an unsubstituted or substituted $C_{1-8}$alkyl, $C_{6-12}$aryl or $C_{7-12}$aralkyl as defined above. In one embodiment, the substituted $C_{1-8}$alkyl is a $C_{1-8}$-haloalkyl including (but not limited to) —$CF_3$ and —$C_2F_5$.

In one embodiment of structure (I) above, $R_2$ is $R_{2a}$ and $R_4$ is $R_{4a}$. In this embodiment, $R_{4a}$ is selected from hydrogen, halogen and an unsubstituted or substituted $C_{1-8}$alkyl, $C_{6-12}$aryl, $C_{7-12}$aralkyl, $C_{3-12}$heterocycle or $C_{4-16}$heterocyclealkyl; and $R_{2a}$ selected from the following chemical moieties (v) through (viii):

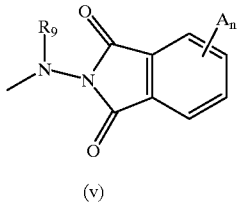

(v)

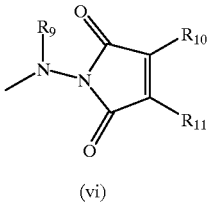

(vi)

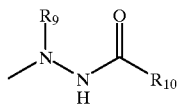

(vii)

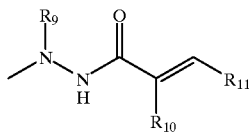

(viii)

wherein $R_9$ is selected from hydrogen, —C(=O)—D—$R_7$ and an unsubstituted $C_{1-8}$alkyl or $C_{7-12}$aralkyl; and $R_{10}$ and $R_{11}$ are the same or different and independently selected from hydrogen and an unsubstituted or substituted $C_{1-8}$alkyl or $C_{6-12}$aryl; n is an integer from 0 to 4 and represents the number of substituents on the benzene ring of chemical moiety (iv); D represents a direct bond, —O— or —NH—; and each occurrence of A is independently selected from a substituent as identified above. In a preferred embodiment, D is a direct bond; R, is selected from hydrogen, —$CH_3$, —$CH_2CH_3$ and —$CH_2C_6H_5$; $R_{10}$ and $R_{11}$ are the same or different and independently selected from hydrogen, —$CH_3$, —$CF_3$, —$(CH_2)_{1-5}CH_3$, —$C_6H_5$, —$CH_2C_6H_5$, and a substituted phenyl or benzyl moiety; and n is 0.

In another embodiment of structure (I) above, $R_2$ is $R_{2b}$ and $R_4$ is $R_{4b}$. In this embodiment, $R_{2b}$ is selected from hydrogen, halogen and an unsubstituted or substituted $C_{1-8}$alkyl, $C_{6-12}$aryl, $C_{7-12}$aralkyl, $C_{3-12}$heterocycle or $C_{4-16}$heterocyclealky $R_{4b}$ is selected from chemical moieties (v) through (viii) identified above.

As used herein, a "$C_{3-12}$heterocycle" is a moiety that contains a ring made up of more than one kind of atom, and which contains 3 to 12 carbon atoms. In one embodiment, the $C_{3-12}$heterocycle is selected from (but not limited to) pyrrolyl, furanyl, thienyl, imidazolyl, oxazolyl, thiazolyl, pyrazolyl, pyrrolidinyl, pyridinyl, pyrimidinyl, purinyl, and thianaphthyl.

A "$C_{4-6}$heterocyclealkyl" is a moiety that contains a $C_{3-12}$heterocycle linked to a $C_{1-8}$alkyl, and which contains 4 to 16 carbon atoms. In one embodiment, the $C_{4-16}$heterocyclealkyl is a methylene furan having the following structure:

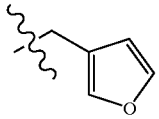

A "substituted" $C_{3-12}$heterocycle or $C_{4-16}$heterocyclealkyl is a —$C_{3-12}$heterocycle or $C_{4-16}$heterocyclealkyl having one or more hydrogens replaced with a substituent selected from halogen (including —F, —Cl, —Br and —I), —OH, —R, —OR, —COOH, —COOR, —COR, —CONH$_2$, —NH$_2$, —NHR, —NRR, —NO$_2$, —SH, —SR, —SOOR, —SO$_3$R and —SOR, where each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl as defined above.

In structure (I) above, $R_6$ is selected from hydrogen, —$CH_3$, —$CH_2C_6H_5$, —F and —$CF_3$.

In one embodiment, the compounds of this invention have structure (I) above wherein $R_5$ is the chemical moiety (i). In this embodiment, the compounds disclosed herein have the following structures (II) and (III):

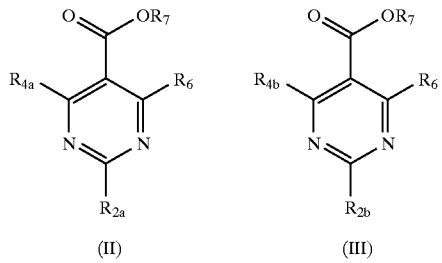

(II)            (III)

wherein $R_{2a}$, $R_{2b}$, $R_{4a}$, $R_{4b}$, $R_6$ and $R_7$ are as defined above.

In a preferred embodiment, the compounds of this invention have structure (II) above, wherein $R_{2a}$, $R_{4a}$, $R_6$ and $R_7$ are selected from the moieties identified in Table 1 below.

TABLE 1

Compounds of Structure (II)

| $R_{2a}$ | $R_{4a}$ | $R_6$ | $R_7$ |
|---|---|---|---|
| (pyrrole-dione-CH$_3$ structure) | —Cl<br>—CF$_3$<br>—CH$_3$<br>-phenyl<br>—(CH$_2$)$_{1-2}$CH$_3$<br>—C$_2$F$_3$ | —H<br>—CF$_3$<br>—CH$_3$ | —CH$_3$<br>—CH$_2$CH$_3$<br>—H |
| (pyrrole-dione-C$_6$H$_5$ structure) | (substituted phenyl X,Y,Z) | | |
| (pyrrole-dione-diCH$_3$ structure) | (thiophene-S-X) | | |
| (phthalimide structure) | | | |

TABLE 1-continued

Compounds of Structure (II)

| $R_{2a}$ | $R_{4a}$ | $R_6$ | $R_7$ |
|---|---|---|---| wherein X, Y and Z are the same or different, and independently selected from hydrogen, —OH, —R, —OR, —COOH, —COOR, —COR—CONH$_2$, —NH$_2$, —NHR, —NRR, —NO$_2$, —SH, —SR, —SOOR, —SO$_3$R and —SOR, where each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl.

In a further preferred embodiment, the compounds of this invention have structure (III) above, wherein $R_{2b}$, $R_{4b}$, $R_6$ and $R_7$ are selected from the moieties identified in Table 2 below.

TABLE 2

Compounds of Structure (III)

| $R_{2b}$ | $R_{4b}$ | $R_6$ | $R_7$ |
|---|---|---|---|
| —Cl<br>—CF$_3$<br>—CH$_3$<br>-phenyl<br>—(CH$_2$)$_{1-2}$CH$_3$<br>—C$_2$F$_3$ | | —H<br>—CF$_3$<br>—CH$_3$ | —CH$_3$<br>—CH$_2$CH$_3$<br>—H |

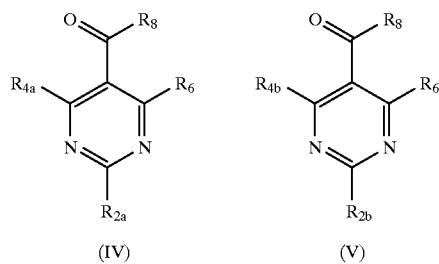

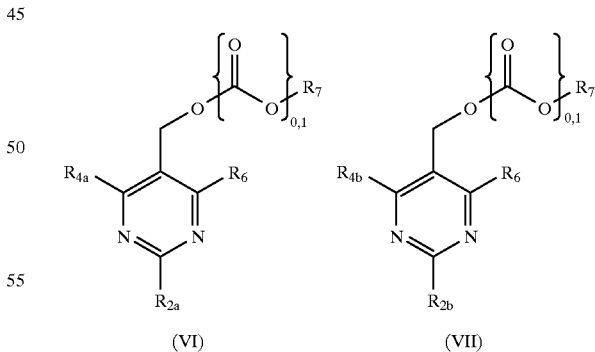

TABLE 2-continued

Compounds of Structure (III)

| $R_{2b}$ | $R_{4b}$ | $R_6$ | $R_7$ |
|---|---|---|---| wherein X, Y and Z are the same or different, and independently selected from hydrogen, —OH, —R, —OR, —COOH, —COOR, —COR—CONH$_2$, —NH$_2$, —NHR, —NRR, —NO$_2$, —SH, —SR, —SOOR, —SO$_3$R and —SOR, where each occurrence of R is independently selected from an unsubstituted or substituted $C_{1-8}$alkyl, $C_{6-12}$aryl, $C_{7-12}$aralkyl, $C_{3-12}$heterocycle or $C_{4-16}$heterocyclealkyl.

In another embodiment, the compounds of this invention have structure (I) above wherein $R_5$ is the chemical moiety (ii). In this embodiment, the compounds disclosed herein have the following structures (IV) and (V):

wherein $R_{2a}$, $R_{2b}$, $R_{4a}$, $R_{4b}$, $R_6$ and $R_8$ are as defined above.

In another embodiment, the compounds of this invention have structure (I) above wherein Rs is the chemical moiety (iii). In this embodiment, the compounds disclosed herein have the following structures (VI) and (VII):

wherein $R_{2a}$, $R_{2b}$, $R_{4a}$, $R_{4b}$, $R_6$ and $R_7$ are as defined above.

In another embodiment, the compounds of this invention have structure ( ) above wherein $R_5$ is the chemical moiety (iv). In this embodiment, the compounds disclosed herein have the following structures (VIII) and (IX):

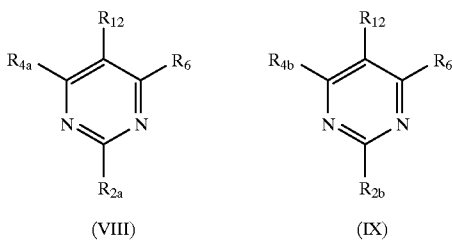

(VIII)          (IX)

wherein $R_{2a}$, $R_{2b}$, $R_{4a}$, $R_{4b}$, $R_6$ and $R_{12}$ are as defined above.

In one embodiment, the compounds of this invention have structure (II) or (III) above and include (but are not limited to) the following: ethyl 2-(N-(1'-aminocitraconamido))-4-trifluoromethylpyrimidine-5-carboxylate; ethyl 2-(N-(1'-aminophthalimido))-4-trifluoromethylpyrimidine-5-carboxylate; 5-acetyl-2-(N-(1'-aminocitraconamido))-4-trifluoromethylpyrimidine; ethyl 2-(N-(1'-amino-3'-phenylmaleimide))-4-trifluoromethylpyrimidine-5-carboxylate; ethyl 2-(N-(1'-amino-3',4'-dimethylmaleimido))-4-trifluoromethylpyrimidine-5-carboxylate; ethyl 2-(N-(1'-aminocitraconamido)-N-methyl)-4-trifluoromethylpyrimidine-5-carboxylate; ethyl 4-(N-(1'-amino-3'-phenylmaleimido))-2-trifluoromethylpyrimidine-5-carboxylate; ethyl 4-(N-(1'-amino-3',4'-dimethylmaleimido))-2-trifluoromethylpyrimidine-5-carboxylate; ethyl 2-(N-(1'-aminocitraconamido))-4-methylpyrimidine-5-carboxylate; ethyl 2-(N-(1-aminocitraconamido))-4-pentafluoroethylpyrimidine-5-carboxylate; ethyl 2-(N-(1'-aminocitraconamido))-4-phenylpyrimidine-5-carboxylate; methyl 2-(N-(1'-aminocitraconamido))-4-(3'-pyridyl)pyrimidine-5-carboxylate; diethyl 2-(N-(1'-aminocitraconamido))pyrimidine-4,5-dicarboxylate; ethyl 2-[N-(1-amino-3'-methylsuccinimido)]-4-trifluoromethyl-pyrimidine-5-carboxylate; methyl 2-[N-(1'-amino-3'-methylsuccinimido)]-4-trifluoromethyl-pyrimidine-5-carboxylate; ethyl 2-[N-(1'-amino-4'-methylphthalimido)]-4-trifluoromethyl-pyrimidine-5-carboxylate; ethyl 2-[N-(1'-amino-3,4-dichlorophthalimido)]-4-trifluoromethyl-pyrimidine-5-carboxylate; ethyl 2-[N-1'-aminocitraconamido)]-pyrimidine-5-carboxylate; ethyl 2-[N-(1'-aminocitraconamido)]-4-ethyl-pyrimidine-5-carboxylate; ethyl 2-[N-(1'-aninocitraconamido)-N-methyl]-4-ethyl-pyrimidine-5-carboxylate; ethyl 2-[N-acetyl-N-(1'-aminocitraconamido)]-4-propyl-pyrimidine-5-carboxylate; ethyl 2-[N-acetyl-N(1'-aminocitraconamido)]-4-trifluoromethyl-pyrimidine-5-carboxylate; methyl 2-[N-(1'-aminocitraconamido)]-4-pentafluoroethylpyrimidine-5-carboxylate; methyl 2-[N(methyl)-N-(1'-amino-3'-methylmaleimido)]-4-pentafluoroethylpyriidine-5-carboxylate; t-butyl-2-[N-(1'-aminocitraconamido)]-4-trifluoromethyl-pyrimidine-5-carboxylate; methyl-2-[N-(1'-aminocitraconamido)]-4-trifluoromethyl-pyrimidine-5-carboxylate; methyl-2-[N-(1'-aninocitraconamido)-N-methyl]4-trifluoromethyl-pyrimidine-5-carboxylate; methyl 2-[N-(1'-aminocitraconamido)]-4-(2'-thienyl)pyrimidine-5-carboxylate; ethyl 2-[N-(1'-aminocitraconamido)-N-benzyl]-4-trifluoromethyl-pyrimidine-5-carboxylate; ethyl 2-[N-(1'-aminocitraconamido)-N-methyl]-4-(2'-thienyl)pyrimidine-5-carboxylate; 2-[N-(1'-aminocitraconamido)]-4-trifluoromethyl-pyrimidine-5-carboxylic acid; ethyl 2-[N-(1'-aminocitraconamido)]-4-(3'-thienyl)pyrimidine-5-carboxylate; ethyl 2-[N-(1'-aminocitraconamido)-N-methyl]-4-(3'-thienyl)pyrimidine-5-carboxylate; ethyl 2-[N-(1'-aminocitraconamido)]-4-(5'-methyl-2'-thienyl)pyrimidine-5-carboxylate; ethyl 2-[N-(1'-aminocitraconamido)]-4-(2'-furanyl)pyrimidine-5-carboxylate; ethyl 2-[N-(1'-aminocitraconamido)-N-methyl]-4-(5'-methyl-2'-thienyl)pyrimidine-5-carboxylate; ethyl 2-[N-(1'-amino-3'-methylmaleimido)]-4-(2'-thianaphthyl)pyrimidine-5-carboxylate; methyl-2-[N-(1'-aminocitraconamido)-N-ethyl]-4-trifluoromethyl-pyrimidine-5-carboxylate; ethyl 2-[N-(1'-aminocitraconamido)-N-butanoyl]-4-trifluoromethyl-pyrimidine-5-carboxylate; ethyl 2-[N-(1'-aminocitraconamido)-N-(N-methylcarboxamidyl)-]-4-trifluoromethylpyrmdine-5-carboxylate; ethyl 2-[N-(1'-aminocitraconamido)-N-(1-oxo-2-phenylethyl)]-4-trifluoromethylpyrimidine-5-carboxylate; ethyl 2-[N-(1'-aminocitraconamido)]-4-methoxymethylpyrimidine-5-carboxylate; ethyl 2-[N-(1'-aminocitraconamido)-N-(ethoxyarbonyl)]-4-trifluoromethylpyrimidine-5-carboxylate; ethyl 2-[N-(1'-aminocitraconamido)-N-benzoyl]-4-trifluoromethylpydine-5-carboxylate; ethyl-2-[N-(1'-aminocitraconamido)-N-methyl]-4-pentafluoroethyl-pyrimidine-5-carboxylate; ethyl 2-[N-(1'-aminocitraconamido)]-4-(2'-thianaphthyl)pyrimidine-5-carboxylate; ethyl 2-[N-(1'-aminocitraconamido)]-4-(2'-thiazolyl)pyrimidine-5-carboxylate; ethyl 2-[N-(1'-aminocitraconamido)-N-methyl]-4-(2'-thiazolyl)pryrimidine-5-carboxylate; ethyl 2-[N-(1'-aminocitraconamido)]-4-cyclopropylpyrimidine-5-carboxylate; and ethyl 2-[-N-(1'-aminocitraconamido)-N-methyl]-4-cyclopropylpyrimidine-S-carboxylate.

In another embodiment, the compounds of this invention have structure (IV) or (V) above and include (but are not limited to) the following: 5-benzoyl-2-chloro-4-trifluoromethylpyrimidine; 5-acetyl-2-[N-(1'-aminocitraconamide)]-4-trifluoromethylpyrimidine; 5-benzoyl-2-[N-(1'-aminocitraconamido)]-4-trifluoromethylpyrimidine; 5-benzoyl-2-[N-(1'-aminocitraconamido)]-4-ethylpyrimidine; 5-benzoyl-2-[N-(1'-aminocitraconamido)-N-methyl]-4-ethylpyrimidine; and 5-butanoyl-2-[N-(1'-aminocitraconamido)-N-methyl]-4-ethylpyrimidine.

In yet another embodiment, the compounds of this invention have structures (VI) or (VII) above, and include (but are not limited to) the following: 5-methylol-2-[-(1'-aminocitraconamido)]-4-ethylpyrimidine; 5-methylol-2-[N-(1'-aminocitraconamido)-N-methyl]-4-ethylpyrimidine; 5-methoxymethane-2-[N-(1'-aminocitraconamido)-N-methyl]-4-ethylpyrimidine; 5-methoxymethane-2-[N-(1'-aminocitraconamido)]-4-trifluoromethylpyrimidine; and 5-ethoxymethylcarbonate-2-[N-(1'-aminocitraconamido)]-4-trifluoromethylpyrimidine.

In still a further embodiment, the compounds of this invention have structures (VIII) or (IX) above, and include (but are not limited to) the following: 2-[N-(1'-aminocitraconamido)-N-methyl]-4-ethyl-5-[2"-(4"-methyl)oxazolyl]pyrimidine; 2-[N-(1'-aminocitraconamido)-N-methyl]-5-[2"-(4"-methyl)oxazolyl]-4-(2'"-thienyl)pyrimidine; 2-[N-(1'-aminocitraconamido)-N-methyl]-4-ethyl-5-[5"-methyl-1",2",4"-oxadiazolyl]pyrimidine; 4-[N-(1'-aminocitraconamido)]-5-(3"-methylisoxazol-5'-yl)-2-(2'"-thienyl)pyrimidine; 4-[N(1'-aminocitraconamido)-5-(N-methyl tetrazolyl)-2-(2"-thienyl) pyrimidine; 4-[N(1'-aminocitraconamido)]-5-(4'-methyloxazol-2-yl)-2-(2'"-thienyl) pyrimidine; 4-[N-(1'-aminocitraconamido)]-5-(4", 5"-dihydro-2"-oxazolyl)2-(2'"-thienyl)pyrimidine; 4-[N-(1'-aminocitraconamido)]-5-(5"-methyl-1",3",4"-oxadiazol-2"-yl)-2-(2'"-thienyl)pyrimidine; and 4-[N-(1'-aminocitraconamido)]-5-cyano-2-(2"-thienyl)pyrimidine.

Preferred compounds of the invention are ethyl 2-(N-(1'-aminocitraconamido))-4-trifluoromethylpyrimidine-5-carboxylate; ethyl 2-N-(1'-aminophthalimido))-4-trifluoromethylpyrimidine-5-carboxylate; 5-acetyl-2-(N-(1'-aminocitraconamido))-4-trifluoromethylpyrimidine-5-carboxylate; ethyl 2-(N-(1'-amino-3'-phenylmaleimido))-4-trifluoromethylpyrimidine-5-carboxylate; ethyl 2-(N-(1'-amino-3',4'-dimethylmaleimido))-4-trifluoromethylpyrimidine-5-carboxylate; ethyl 2-(N-(1'-aminocitraconamido)-N-methyl)-4-trifluoromethylpyrimidine-5-carboxylate; ethyl 4-(N-(1'-amino-3'-phenylmaleimido))-2-trifluoromethylpyrimidine-5-carboxylate; ethyl 4-(N-(1'-amino-3',4'-dimethylmaleimido))-2-trifluoromethylpyrmidine-5-carboxylate; ethyl 2-(N-(1'-aminocitraconamido))-4-methylpyrimidine-5-carboxylate; ethyl 2-(N-(1'-aminocitraconamido))-4-pentafluoroethylpyrimidine-5-carboxylate; ethyl 2-(N-(1'-aminocitraconamido))-4-phenylpyrimidine-5-carboxylate; methyl 2-(N-(1'-aminocitraconamido))-4-(3'-pyridyl)pyrimidine-5-carboxylate; diethyl 2-(N-(1'-aminocitraconamido))pyrimidine-4,5-dicarboxylate; ethyl 2-(N-(1'-aminocitraconamido))-4-(2'-thienyl)pyrimidine-5-carboxylate; ethyl 2-(N-(1'-aminocitraconamido)-N-methyl)-4-ethylpyrimidine-5-carboxylate; methyl 2-(N-(1'-aminocitraconamido))-4-(2'-thienyl)pyrimidine-5-carboxylate; ethyl 2-(N-(1'-aminocitraconamido)-N-methyl)-4-(2'-thienyl)pyrimidine-5-carboxylate; ethyl 2-(N-(1-aminocitraconamido))-4-(5'-methyl-2'-thienyl)pyrimidine-5-carboxylate; ethyl 4-(N-(1'-aminocitraconamido))-2-phenylpyrimidine-5-carboxylate; and ethyl 4-(N-(1'-aminocitraconamido))-2-(2'-thienyl)pyrimidine-5-carboxylate.

The compounds of this invention further include pharmaceutically and prophylactically acceptable salts of compounds of structure (I). Compounds of structure (I) may contain proton donating groups (e.g., a carboxylic acid group) and/or proton accepting groups (e.g., a group with a nitrogen atom having a free lone pair of electrons, such as an amine group), and the salts of compounds of structure (I) may be formed and utilized in the practice of the invention. Thus, compounds of the invention may be in the form of a base addition salt (i.e., a salt of a proton donating group) or in the form of an acid addition salt (i.e., a salt of a proton accepting group), as well as the free acid or free base forms thereof.

Acid addition salts of a free base amino compound of the invention may be prepared by methods well known in the art, and may be formed from organic and inorganic acids. Suitable organic acids include acetic, ascorbic, benzenesulfonic, benzoic, fumaric, maleic, methanesulfonic, and succinic acids. Suitable inorganic acids include hydrochloric, hydrobromic, sulfuric, phosphoric and nitric acids. Base addition salts of a free acid carboxylic acid compound of the invention may also be prepared by methods well known in the art, and may be formed from organic and inorganic bases. Thus, the compounds of this invention also include those salts derived from inorganic bases such as the hydroxide or other salt of sodium, potassium, lithium, ammonium, calcium, magnesium, iron, zinc, copper, manganese, aluminum, and the like, and organic bases such as substituted ammonium salts.

The compounds of this invention may be made by one skilled in organic synthesis by known techniques, as well as by the synthetic routes disclosed herein. Referring to FIG. 1, the compounds of this invention may be made from commercially available β-keto esters 1 by heating at elevated temperatures (75–110° C.) with a mixture of urea and triethylorthoformate (or a substituted orthoformate) to provide ureido derivatives 2. Treatment of these intermediates with sodium alkoxides, such as sodium ethoxide in an alcoholic solvent at 35–100° C., gives 2-hydroxypyrimidine esters 3 which, upon treatment with a chlorinating agent such as phosphorous oxychloride at elevated temperatures (75–120° C.), yields 2-chloropyrimidine esters 4.

Compound 4 may be reacted with various nucleophiles in an aprotic solvent at ambient temperature to provide derivatives 7. Compound 4 may also be converted to the carbonyl chloride 5 by treatment with base, such as hydroxide in water, followed by a chlorinating agent, such as oxalyl chloride in methylene chloride. Compound 5 can be treated with an organometallic, such as methyl magnesium bromide: in a solvent such as THF or ether at −35° C. to −65° C., to give ketone 9. This ketone may be treated with various nucleophiles in an aprotic solvent and at ambient temperature to provide compound 10.

Alternatively, compound 3 may be converted to the hydroxy carboxylic acid 6 by treatment with a strong base, such as sodium hydroxide, or strong acid, such as HCl, at elevated temperature (70–110° C.). The hydroxy carboxylic acids may be converted to the chloro carbonyl chloride with thionyl chloride and/or phosphorous oxychloride.

Compound 4 can also be treated with hydrazine at ambient temperature in a solvent, such as THF, with pyridine as a catalyst to provide the intermediates of structure 8. These hydrazino derivatives can be reacted with cyclic anhydrides, such as citraconic anhydride, in a solvent, such as chloroform, at elevated temperatures (35–65° C.) to provide compounds of structure 11. Subsequent treatment of 11 with a strong base, such as sodium hydride, in an aprotic solvent, such as THF, at ambient temperature followed by an alkyl iodide, such as methyl iodide, provides the alkylated derivatives of structure 12.

Compounds of structures (VI) and (VII) may be prepared by reducing any of the compounds in FIG. 1 so as to convert a carboxylate group to a methylol (—CH$_2$OH) group. Lithium aluminum hydride is a suitable reducing agent. In any event, the methylol group may, if desired, be converted to —CH$_2$OR$_7$ by standard alkylation chemistry (e.g., using a strong base and a nucleophile).

Figure 2:
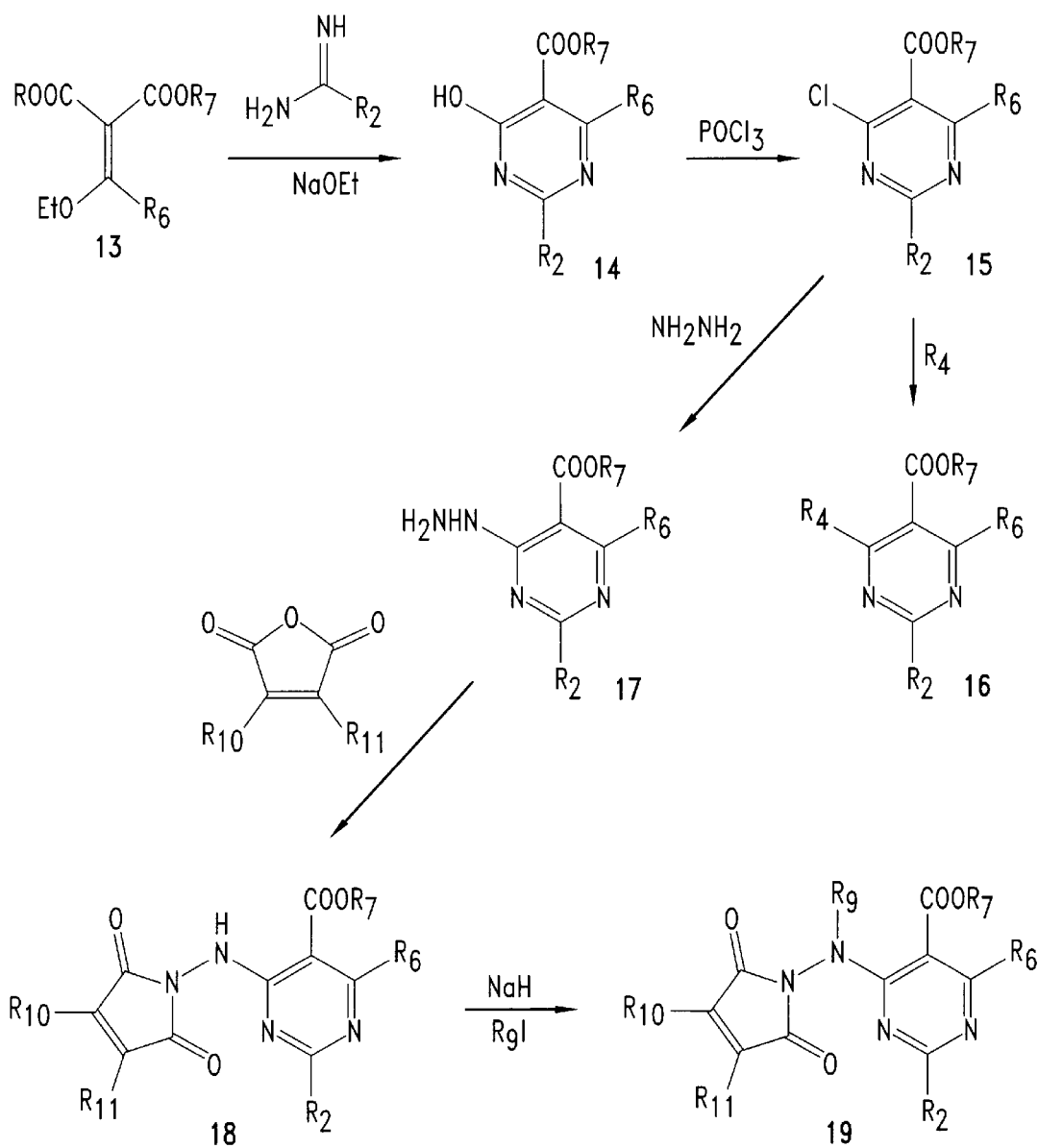
Figure 3:
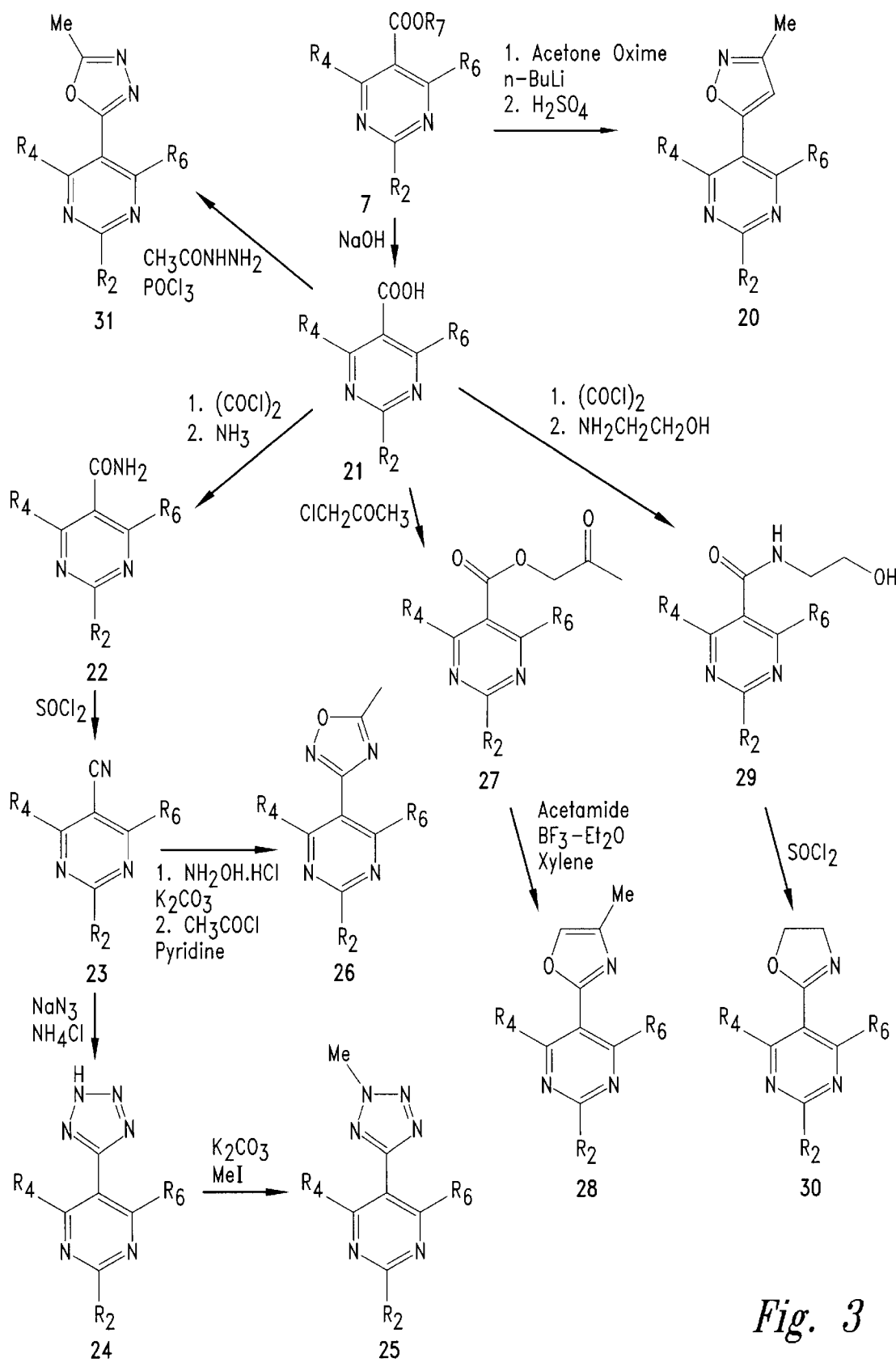

Referring to FIG. 2, an alternative synthetic procedure is disclosed. In this procedure, commercially available diethyl ethoxymethylenemalonate 13 is treated with an amidine, such as trifluoromethylamidine, in a protic solvent, such as ethanol, in the presence of an alkoxide, such as NaOEt, at elevated temperatures (75–110° C.) to give the hydroxy pyrimidine ester 14. Chlorination with a chlorinating agent, such as POCl$_3$ or thionyl chloride, yields the chloroester derivative 15 which can be treated R.oth various amines at ambient temperature in an aprotic solvent, such as THF, to provide the substituted pyrimidines 16. Derivative 15 may also be treated with hydrazine in a solvent such as THF in the presence of pyridine to give the hydrazino intermediates 17. Treatment of 17 with various cyclic anhydrides, such as citraconic anhydride, in a solvent, such as chloroform, at elevated temperatures (34–65° C.) provide compounds, of structure 18. Alkylation of these compounds with a hydride, such as sodium hydride, followed by an alkyl halide in an aprotic solvent, such as THF, gives the alkylated derivatives of structure 19.

Again, compounds of structures (VI) and (VII) may be prepared from the corresponding carboxylate compounds as discussed above in connection with FIG. 1. Compounds of the invention wherein R is —C(=O)R₇ may be prepared from the corresponding compound wherein R is hydrogen (as prepared according to either of FIG. 1 or 2) using standard acylation chemistry. For example, a compound having $R_9$ equal to hydrogen may be treated with a strong base (e.g., NaH), followed by an acylating agent (e.g., Cl—C(=O)R₇).

Once synthesized, the compounds of this invention may be formulated for administration to a warm-blooded animal by a variety of techniques known to those skilled in the art. In one embodiment, the compound is in the form of a pharmaceutical composition for prophylactic or therapeutic use, and which contains at least one compound of this invention in combination with a pharmaceutically acceptable carrier or diluent. The compound is present in the composition in an amount which, upon administration to the animal, is effective in preventing or treating the condition of interest. Preferably, the composition includes a compound of this invention in an amount ranging from 0.01 mg to 250 mg per dosage, depending upon the route of administration, and more preferably from 1 mg to 60 mg. Appropriate concentrations, dosages and modes of administration may be readily determined by one skilled in the art.

Suitable carriers or diluents are familiar to those skilled in the formulation field. For compositions formulated as liquid solutions, acceptable carrier or diluents include saline and sterile water, and may optionally include antioxidants, buffers, bacteriostats and other common additives. The compositions of this invention may also be formulated as pills, capsules, granules or tablets which contain, in addition to the compound of this invention, diluents, dispersing and surface active agents, binders and lubricants. One skilled in the art may further formulate the compounds of this invention in any appropriate manner, and in accordance with accepted practices, such as those disclosed in *Remington's Pharmaceutical Sciences*, Gennaro, Ed., Mack Publishing Co., Easton, Pa., 1990 (incorporated herein by reference).

In another embodiment, the present invention provides methods for preventing or treating a variety of conditions. Such methods include administering a compound of this invention to a warm-blooded animal in need thereof in an amount sufficient to prevent or treat the condition. Such methods include systemic administration of a compound of this invention, preferably in the form of a composition as disclosed above. As used herein, systemic administration includes oral and parental methods of administration. For oral administration, suitable pharmaceutical compositions include powders, granules, pills, tablets and capsules, as well as liquids, syrups, suspensions and emulsions. These compositions may also include flavorants, preservatives, suspending, thickening and emulsifying agents, and other pharmaceutically acceptable additives. For parental administration, the compounds of the present invention may be prepared in aqueous injectable solutions which may contain, in addition to the compound of this invention, buffers, antioxidants, bacteriostats and other additives commonly employed in such solutions.

As mentioned above, compounds of the present invention can be used to prevent or treat a wide variety of disorders, diseases and/or illnesses. In particular, the compounds may be administered to a warm-blooded animal for prevention or treatment of rheumatoid arthritis, osteoarthritis, tissue and/or organ transplant rejection, sepsis, ARDS, asthma, trauma, oxidative stress, cell death, irradiation damage, ischemia, reperfusion, cancer, viral infection, and autoimmune diseases such as psoriasis, inflammatory bowel disease, glomerulonephritis, lupus, uveitis and chronic hepatitis.

Compounds of this invention may be screened by known and accepted techniques for their ability to function as prophylactically and/or therapeutically active agents. For example, the compounds may be evaluated in in vitro and/or in vivo assays indicative of the compound's anti-inflammatory and immunosuppressive properties. To this end, such compounds may first be evaluated in a number of cell-based assays which determine the ability of a compound to prevent activation of NFκB and AP-1 (see Example 126). Next, the compound's ability to attenuate cytokine levels (such as IL-2 and IL-8), which are known to be elevated in certain disease states, may be determined (see Example 127). The compounds may then be evaluated in an appropriate animal model, including rodent models of inflammation and immunosuppression (see Example 128).

It should be recognized that, for example, in the case of immunosuppressive drugs and other agents which have utility for the treatment of rheumatoid arthritis (RA), numerous studies have been performed directed to the activity of such drugs. To this end, cyclosporin A has been used in clinical trials since the late 1970's as a second-line drug, and is recommended to be used only in patients with active RA. Thus, Experiment 128 may be performed utilizing cyclosporin A as a positive control. A recent review of such immunosuppressive drugs, including relevant assays for the same, is presented by R. P. Carlson in *Exp. Opin. Invest. Drugs* 4(9):853–859, 1995 (incorporated herein by reference in its entirety, including cited references).

The following examples are presented for purpose of illustration, not limitation.

EXAMPLES

To summarize the examples that follow, Examples 1–143 disclose the synthesis of representative compounds of this invention, as well as intermediates thereto; Example 144 discloses the synthesis of representative compounds by combinational chemistry techniques; Examples 145–146 disclose the ability of representative compounds of this invention to inhibit NFκB, AP-1 and cytokines; and Example 147 discloses assays for evaluating activity of representative compounds of this invention in both graft versus host disease and contact sensitivity models.

Example 1

2-CHLORO-5-[3',5'-BIS(TRIFLUOROMETHYL) PHENACYL]-4-TRIFLUOROMETHYLPYRINIDINE

To magnesium turnings (0.026 g, 1.06 mmol) in Et₂O (15 mL) was added a solution of 3,5-bistrifluoromethyl iodobenzene (0.300 g; 0.882 mmol) in Et₂O (5 mL). The reaction was refluxed under an atmosphere of N₂ for 2 h and then cooled to 0° C. A solution of 2-chloro-4-trifluoromethylpyrimidine-5-carbonyl chloride (0.205 g, 0.838 mmol) in Et₂O (5 mL) was added dropwise via syringe. After stirring 1 hour at 0° C., water (15 mL) was added and the mixture extracted with Et₂O (2×20 mL). The organic layer was washed with brine (15 mL), dried over MgSO₄, filtered and concentrated. The residue was chromatographed (SiO₂, hexanes/EtOAc 8:1) to give the title compound (0.078 g, 21% yield) as an oil; ¹H NMR (CDCl₃) δ 8.90 (s, 1H), 8.21 (s, 1H), 8.19 (s, 2H).

Example 2

5-BENZOYL-2-CHLORO-4-TRIFLUOROMETHYLPYRIMIDINE

The title compound was prepared as described in Example 1, but employing phenyl magnesium bromide (0.23 mL, 0.69 mmol) and the acid chloride (0.17 g, 0.69 mmol), resulting in a yield of 30%; $^1$H NMR (CDCl$_3$) δ 8.81 (s, 1H), 7.4–7.8 (m, 5H).

Example 3

ETHYL UREIDOMETHYLENE ACETOACETATE

A mixture of ethyl acetoacetate (200 g, 1.54 mole), urea (105 g, 1.54 mole) and triethyl orthoformate (228 g, 1.54 mole) was heated at 140° C. under N$_2$ for 22 h. The reaction mixture was cooled and filtered to provide the title compound in a 51% yield (156 g); m.p. 173–174° C.

Example 4

ETHYL UREIDOMETHYLENE BENZOYLACETATE

The title compound was prepared as described in Example 3, but employing ethyl benzoylacetate (30.0 g, 156 mmol), resulting in a yield of 21% (12 g); m.p. 124–126° C.

Example 5

ETHYL 2-HYDROXY-4-METHYLPYRIMIDINE-5-CARBOXYLATE

A solution of ethyl ureidomethylene acetoacetate (50 g, 250 mmol) NaOEt (22.1 g, 325 mmol) in EtOH (500 mL) was stirred at room temperature under N$_2$ for 3 days. The resulting solid was filtered and dried to yield the title compound as a sodium salt in a yield of 88% (45 g); m.p.>220° C. (dec.).

Example 6

ETHYL 2-HYDROXY-4-PHENYLPYRIMIDINE-5-CARBOXYLATE

The title compound was prepared as described in Example 5, but employing ethyl ureidomethylene benzoyl acetate (12 g, 45 mmol), resulting in a yield of 15% (6 g); m.p.>260° C., (dec.).

Example 7

ETHYL 2-CHLORO-4-METHYLPYRIMIDINE-5-CARBOXYLATE

A solution of ethyl 2-hydroxy-4-methylpyrimidine-5-carboxylate (5 g, 27.5 mmol) and POCl$_3$ (84 g, 550 mmol) was heated at reflux under N$_2$ for 1 h. The reaction was cooled and concentrated. The residue was partitioned between CHCl$_3$ and H$_2$O and the organic layer was dried (Na$_2$SO$_4$), filtered, and concentrated to yield the title compound in a yield of 27% (1.5 g); $^1$H NMR (CDCl$_3$) δ 9.04 (s, 1H), 4.42 (q, 2H), 2.85 (s, 3H), 1.43 (t, 3H).

Example 8

ETHYL 2-CHLORO-4-PHENYLPYRIMIDINE-5-CARBOXYLATE

The title compound was prepared as described in Example 7, but employing 2-hydroxy-4-phenylpyrimidine-5-carboxylate (6 g, 25 mmol) to give the title compound (5.5 g, 86%); m.p. 45–47° C.

Example 9

2-CHLORO-4-METHYLPYRIMIDINE-5-CARBOXYLIC ACID

A solution of ethyl 2-chloro-4-methylpyrimidine-5-carboxylate (1.0 g, 5 mmol), NaOH (0.24 g, 6 mmol) in H$_2$O (30 mL) was stirred at room temperature for 3 h. The solution was acidified with 6N HCl and the resulting solid was filtered and dried to give the title compound (0.67 g 78%), $^1$H NMR (DMSO-d$_6$) δ 9.01 (s, 1H), 2.75 (s, 3H).

Example 10

2-CHLORO-4-PHENYLPYRIMIDINE-5-CARBOXYLIC ACID

The title compound was prepared as described in Example 9, but employing 2-chloro-4-phenylpyrimidine-5-carboxylate (4.5 g, 17 mmol), resulting in a yield of 87% (3.9 g); m.p. 105–110° C.

Example 11

2-CHLORO-4-METHYLPYRIMIDINE-5-CARBONYL CHLORIDE

A solution of 2-chloro-4-methylpyrimidine-5-carboxylic acid (0.81 g, 4.70 mmol), oxalyl chloride (0.89 g, 7.05 mmol), DMF (2 drops) in CH$_2$Cl$_2$ (23 mL) was stirred at room temperature under N$_2$ for 4 h. The solution was concentrated and distilled to give the title compound (0.55 g, 61%); b.p. 90–100° C., 1.3 mm/Hg; $^1$H NMR (CDCl$_3$) δ d9.02 (s, 1H), 2.74 (s, 3H).

Example 12

2-CHLORO-4-PHENYLPYRIMIDINE-5-CARBONYL CHLORIDE

The compound was prepared as described above in Example 11, but employing 2-chloro-4-phenylpyrimidine-5-carboxylic acid (3.8 g, 14 mmol), resulting in a yield of 53%; m.p. 42° C.

Example 13

2-CHLOROPYRIMIDINE-5-CARBONYLCHLORIDE

The compound was prepared as described in the literature (see Arukwe, *J. Undheim, K Acta Chemica Scand.* B40:764, 1986).

Example 14

ETHYL ETHOXYMETHYLENE-4,4,4-TRIFLUOROACETOACETATE

A solution of ethyl 4,4,4-trifluoroacetoacetate (46 g, 0.25 mol) triethyl orthoformate (74 g, 0.50 mol) and Ac$_2$O (77 g, 0.75 mol) was heated at 120–140° C. for 7 h. The mixture was concentrated and distilled to give the title compound in a 98% yield (58.6 g); b.p. 80–90° C., 1.5 mm/Hg.

Example 15

ETHYL 2-TRIFLUOROMETHYL-4-HYDROXYPYRIMIDINE-5-CARBOXYLATE

A solution of diethyl ethoxymethylenemalonate (35.0 g, 162 mmol), trifluoroacetaridine (18 g, 162 mmol) and NaOEt (11.0 g, 162 mmol) in EtOH (200 mL) was heated at reflux for 6 h. The reaction mixture was concentrated and H$_2$O (48 naL) was added. The resulting solid was filtered, washed with Et$_2$O (300 mL) and H$_2$O (200 mL), and dried to give the title compound (21 g, 50% yield); m.p.>220° C. (dec.); $^1$H NMR (DMSO-d$_6$) δ 8.38, 4.16 (q, 2H), 1.25 (q, 3H).

Example 16

2-TRIFLURORMETHYL-4-CHLOROPYRIMIDINE-5-CARBONYL CHLORIDE

A solution of ethyl 2-trifluoromethyl-4-hydroxypyrimidine-5-carboxylate (5.00 g, 19.4 mmol) and NaOH (0.93 g, 23.3 mmol) in H$_2$O (20 mL) was stirred at 60° C. for 15 h. The reaction was acidified (concentrated HCl) and concentrated until a solid began to form. The solid was filtered and dried to give 2-trifluoromethyl-4-hydroxypyrimidine-5-carboxylic acid (2.1 g, 53% yield); $^1$H NMR (DMSO-d$_6$) δ 8.83 (s, 1H).

A solution of 2-tifluoromethyl-4-hydroxypyrimidine-5-carboxylic acid (2.0 g, 10.4 mmol), POCl$_3$ (32 g, 212 mmol) and SOCl$_2$ (25 g, 212 mmol) was heated at reflux for 4 days. The reaction was concentrated and distilled (b.p. 90–95° C., 1.5 mm/Hg) to provide the title compound (2.1 g, 81% yield), $^1$H NMR (CDCl$_3$) δ 9.45 (s, 1H).

Example 17

2-CHLORO-4-PENTAFLUOROETHYLPYRIMIDINE-5-CARBONYL CHLORIDE

A solution of ethyl 2-hydroxy-4-pentafluoroethylpyrimidine-5-carboxylate (4.0 g, 13 mmol) and NaOH (1.60 g, 39 mmol) in EtOH (20 mL) and H$_2$O (45 mL) was heated at reflux for 1 h. The solution was cooled and acidified (concentrated HCl). The resulting solid was filtered and dried to provide 2-hydroxy-4-pentafluoroethylpyrimidine-5-carboxylic acid (3.3 g, 98% yield); $^1$H NMR (DMSO-d$_6$) δ 9.90 (bs, 1H), 8.43 (s, 1H).

A solution of 2-hydroxy-4-pentafluoroethylpyrimidine-5-carboxylic acid (3.33 g, 12.9 mmol) in SOCl$_2$ (27.7 g, 233 mmol) was heated at reflux for 0.5 h. Then POCl$_3$ (35.6 g, 233 mmol) was added to the reaction mixture and heating continued for 36 h. The reaction mixture was then concentrated and distilled (b.p. 80–85° C., 1 mm/Hg) to give the title compound (1.2 g, 35% yield); $^1$H NMR (DMSO-d$_6$) δ 9.18 (s, 1H).

Example 18

ETHYL 4-HYDRAZINO-2-TRIFLUOROMETHYLPYRIMIDINE-5-CARBOXYLATE

A solution of ethyl 4-chloro-2-trifluoromethylpyrimidine-5-carboxylate (0.20 g, 0.79 mmol), hydrazine (0.18 g, 6.0 mmol) and THF was stirred for 1 h at room temperature. The solution was filtered and dried to give the title compound in a 96% yield; $^1$H NMR (CDCl$_3$) δ 9.26 (bs, 1H), 8.90 (s, 1H), 4.40 (q, 2H), 4.24 (bs, 2H), 1.41 (t,3H).

Example 19

ETHYL 2-HYDRAZINO-4-TRIFLUOROMETHYLPYRIMIDINE-5-CARBOXYLATE

The title compound was prepared as described in Example 18, but employing ethyl-2-chloro-4-trifluoromethylpyrimidine-5-carboxylate (0.20 g, 0.79 mmol), resulting in a yield of 91% (0.18 g); m.p. 89–90° C.

Example 20

ETHYL 2-[N-(1'-AMINOCITRACONAMIDO)]-4-TRIFLUOROMETHYLPYRIMIDINE-5-CARBOXYLATE

A solution of ethyl 2-hydrazino-4-trifluoromethylpyrimidine-5-carboxylate (0.18 g, 0.72 mmol) and citraconic anhydride (0.08 ml, 0.94 mmol) in CHCl$_3$ (10 ml) was refluxed for 0.5 h. The solution was cooled, concentrated and chromatographed (SiO$_2$, hexanes/EtOAc) to give the title compound (0.10 g, 39% yield); $^1$H NMR (CDCl$_3$) δ 9.94 (s, 1H), 7.72 (s, 1H), 6.53 (s, 1H), 4.41 (q, 2H), 2.19 (s, 3H), 1.36 (t, 3H).

Example 21

ETHYL 4-[N-(1'-AMINOCITRACONAMIDO)]-2-TRIFLUOROMETHYLPYRIMIDINE-5-CARBOXYLATE

The title compound was prepared as described in Example 20, but employing ethyl 4-hydrazino-2-trifluoromethylpyrimidine-5-carboxylate (0.19 g, 0.76 mmol), resulting in an 80% yield (0.21 g); m.p. 85–86° C.

Example 22

ETHYL 2-[N-(1'-AMINOPHTHALIMIDO)]-4-TRIFLUOROMETHYLPYRIMIDINE-5-CARBOXYLATE

A solution of ethyl 2-chloro-4-trifluoromethyl-5-pyrimidine ester (0.25 g, 1.0 mmol), N-aminophthalimide (0.17 g, 1.0 mmol) and pyridine (0.09 ml, 1.0 mmol) in THF was heated at 60° C. for 5 h and then concentrated. The residue was chromatographed (SiO$_2$, hexanes/EtOAc, 1:1) to give the title compound (0.07 g, 17% yield); m.p. 46–48° C.

Example 23

5-ACETYL-2-[N-(1'-AMINOCITRACONAMIDO)]-4-TRIFLUOROMETHYLPYRIMIDINE

To a solution of 2-chloro-4-trifluoromethylpyrimidine-5-carbonyl chloride (0.50 g, 2.0 mmol) in THF at −78° C. under N$_2$ was added MeMgBr (0.75 ml, 2.3 mmol). The reaction was stirred 0.75 h, quenched with H$_2$O (1 ml) and diluted with EtOAc (30 ml). The organic layer was washed with H$_2$O, brine and then dried over MgSO$_4$. The residue was chromatographed (SiO$_2$, hexanes/EtOAc, 2:1) to provide the 5-acetyl-2-chloro-4-trifluoromethylpyrimidine (0.20 g) in 43% yield. The title compound was then prepared as described for ethyl 2-[N-(1'-aminocitraconamide)]-4-trifluoromethylpyrimidine-5-carboxylate of Example 20, resulting in a 29% yield (0.08 g); m.p. 61–62° C.

Example 24

ETHYL UREIDOMETHYLENE PROPIONOYLACETATE

The title compound was prepared as described in Example 3, but employing ethyl propionylacetate (5.15 g, 35.7 mmol), resulting in a yield 43% (3.29 g); m.p. 148–150° C.

Example 25

ETHYL UREIDOMETHYLENE BUTYRYLACETATE

The title compound was prepared as described in Example 3, but employing ethyl butyrylacetate (25 g, 158 mmol), resulting in a yield of 47% (17 g); m.p. 145–147° C.

Example 26

ETHYL UREIDOMETHYLENE 2-THIENYLACETATE

The title compound was prepared as described in Example 3, but employing ethyl 2-thienoylacetate (7.22 g, 36.4 mmol), resulting in a yield of 41% (4.0 g); m.p. 149–150° C.

Example 27

ETHYL 2-HYDROXY-4-ETHYLPYRIMIDINE-5-CARBOXYLATE

The title compound was prepared as described in Example 5, but employing ethyl ureidomethylene ethanoylacetate (2.5 g, 11.7 mmol), resulting in a yield of 52% (1.2 g); $^1$H NMR (DMSO-d$_6$) δ 8.05 (d, 1H), 4.24 (q, 2H), 2.87 (m, 2H), 1.29 (t, 3H).

Example 28

ETHYL 2-HYDROXY 4-PROPYLPYRIMIDINE-5-CARBOXYLATE

The title compound was prepared as described in Example 5, but employing ethyl ureidomethylene propionoylacetate (10.96 g, 48 mmol), resulting in a yield of 73% (7.3 g); $^1$H NMR (CDCl$_3$) δ 8.2 (s, 1H), 4.35 (q, 2H), 3.0 (t, 2H), 1.75 (m, 2H), 1.37 (t, 3H), 1.0 (t, 3H).

Example 29

ETHYL 2-HYDROXY-4-(2'-THIENYL)PYRIMIDINE-5-CARBOXYLATE

The title compound was prepared as described in Example 5, but employing ethyl ureidomethylene 2-thiophenoylacetate (4.0 g, 14.9 mmol), resulting in a yield of 79% (2.9 g); m.p. 144–146° C.

Example 30

ETHYL 2-HLORO-4-ETHYLPYRIMIDINE-5-CARBOXYLATE

The title compound was prepared as described in Example 7, but employing ethyl 2-hydroxy-4-ethylpyrimidine-5-carboxylate (1.2 g, 6.1 mmol), resulting in a yield of 77% (1.0 g); GC/MS calcd for $C_9H_{11}N_2O_2Cl$ (M$^+$) 214, found 214.

Example 31

ETHYL 2-HLORO-4-PROPYLPYRIMIDINE-5-CARBOXYLATE

The title compound was prepared as described in Example 7, but employing ethyl 2-hydroxy-4-propylpyrimidine-5-carboxylate (1.05 g, 5 mmol), resulting in a yield of 79% (0.9 g); GC/MS calcd for $C_{10}H_{13}N_2O_2Cl$ (M$^+$) 228, found 228.

Example 32

ETHYL 2-HLORO-4-(2'-THIENYL)PYRIMIDINE-5-CARBOXYLATE

The title compound was prepared as described in Example 7, but employing ethyl 2-hydroxy-4-(2'-thienyl)pyrimidine-5-carboxylate (1.0 g, 4.0 mmol), resulting in a yield of 19% (0.2 g); GC/MS calcd for $C_{11}H_9N_2O_2SCl$ (M$^+$) 268, found 268.

Example 33

ETHYL 2-HYDRAZINO-4-ETHYLPRYRIMIDINE-5-CARBOXYLATE

The title compound was prepared as described in Example 18, but employing ethyl 2-chloro-4-ethylpyrimidine-5-carboxylate (1 g, 4.7 mmol), resulting in a yield of 41% (0.4 g); GC/MS calcd for $C_9H_{14}N_4O_2$ (M$^+$) 210, found 210.

Example 34

ETHYL 2-HYDRAZINO-4-PROPYLPYRIMIDINE-5-CARBOXYLATE

The title compound was prepared as described in Example 18, but employing ethyl 2-chloro-4-propylpyrimidine-5-carboxylate (0.9 g, 3.9 mmol), resulting in a yield of 97% (0.85 g); GC/MS calcd for $C_{10}H_{16}N_4O_2$ (M$^+$) 224, found 224.

Example 35

ETHYL 2-HYDRAZINO-4-(2'-THIENYL)PYRIMIDINE-5-CARBOXYLATE

The title compound was prepared as described in Example 18, but employing ethyl 2-chloro-4-(2'-thienyl)pyrimidine-5-carboxylate (0.2 g, 0.7 mmol), resulting in a yield of 92% (0.17 g); GC/MS calcd for $C_{11}H_{12}N_4O_2S$ (M$^+$) 264, found 264.

Example 36

ETHYL 2-[N-(1'-AMINOCITRACONAMIDO)]-4-ETHYLPRYRIMIDINE-5-CARBOXYLATE

The title compound was prepared as described in Example 20, but employing ethyl 2-hydrazino-4-ethylpyrimidine-5-carboxylate (0.4 g, 1.9 mmol), resulting in a yield of 32% (0.13 g); $^1$H NMR (CDCl$_3$) δ 8.84 (s, 1H), 6.51 (s, 1H), 5.94 (s, 1H), 4.32 (m, 2H), 3.05 (q, 2H), 2.18 (s, 3H), 1.35 (m, 6H).

Example 37

ETHYL 2-[N-(1'-AMINOCITRACONAMIDO)]-4-PROPYLPYRIMIDME-5-CARBOXYLATE

The title compound was prepared as described in Example 20, but employing ethyl 2-hydrazino-4-propylpyrimidine-5-carboxylate (0.77 g, 3.4 mmol), resulting in a yield of 73% (0.7 g); m.p. 103–105° C.

Example 38

ETHYL 2-[N-(1'-AMINOCITRACONAMIDO)]-4-(2'-THIENYL)PYRIMIDINE-5-CARBOXYLATE

The title compound was prepared as described in Example 20, but employing ethyl 2-hydrazino-4-(2'-thienyl)pyrimidine-5-carboxylate (0.17 g, 0.64 mmol), resulting in a yield of 55% (0.127 g); m.p. 123–126° C.

Example 39

5-AMIDO-2-[N-(1'-AMINOCITRACONAMIDO)]-4-TRIFLUOROMETHYLPYRIMIDINE

To a solution of 2-chloro-4-trifluoromethylpyrimidine-5-carbonyl chloride (0.50 g, 2.0 mmol) in THF at 0° C. under N$_2$ was added 2M NH$_3$/MeOH (1.0 ml, 2.0 mmol). The reaction was stirred 5 minutes, diluted with EtOAc (10 ml), filtered and concentrated. Chromatography (SiO$_2$, hexanes/EtOAc, 4:1) provided the 5-amido-2-chloro-4-trifluoromethylpyrimidine (0.20 g) in 44% yield. The title compound was then prepared as described for ethyl 2-[N-(1'-aminocitraconamide)]-4-trifluoromethylpyrimidine-5-carboxylate, resulting in a 15% yield (0.04 g); $^1$H NMR (CDCl$_3$) δ 8.69 (s, 1H), 8.30 (s, 1H), 6.52 (s, 1H), 6.51 (s, 1H), 6.28 (s, 1H), 2.19 (s, 3H).

Example 40

ETHYL 2-[N-(1'-AMINO-3'-PHENYLMALEIMIDO)]-4-TRIFLUOROMETHYLPYRIMIDINE-5-CARBOXYLATE

The title compound was prepared as described for ethyl 2-[N-(1'-aminocitraconamide)]-4- trifluoromethylpyrimidine-5-carboxylate but employing 3-phenylmaleic anhydride (0.21 g, 1.2 mmol), resulting in a 74% yield (0.18 g); m.p. 52–53° C.

Example 41

ETHYL 2-[N-(1'-AMINO-3',4'-DIETHYLMALEIMIDO)]-4-TRIFLUOROMETHYLPYRIMIDINE-5-CARBOXYLATE

The title compound was prepared as described for ethyl 2-[N-(1'-aminocitraconamido)]-4-trifluoromethylpyrimidine-5-carboxylate but employing 3,4-dimethylmaleic anhydride (0.08 g, 0.63 mmol), resulting in a 47% yield (0.10 g); m.p. 110–111° C.

Example 42

ETHYL 2-[N-(1'-AMINOCITRACONAMIDO)-N-METHYL]-4-TRIFLUOROMETHYLPYRIMIDINE-5-CARBOXYLATE

To a solution of ethyl 2-[N-(1'-aminocitraconamido)]-4-trifluoromethylpyrimidine-5-carboxylate (0.10 g, 0.29 mmol) in THF at 0° C. under nitrogen was added NaH (0.01 g, 0.44 mmol). After 5 minutes, MeI (0.10 ml, 1.6 mmol) was added and the reaction was allowed to warm to room temperature. After stirring 0.5 h at room temperature, the reaction was diluted with EtOAc (15 mL), washed with $H_2O$ and brine. The organic layer was dried over $MgSO_4$, filtered and concentrated. The residue was chromatographed ($SiO_2$, hexanes/EtOAc 8:1) to give the title compound (0.05 g, 60% yield); $^1H$ NMR ($CDCl_3$) δ 9.05 (s, 1H), 6.48 (s, 1H), 4.37 (q, 2H), 3.61 (s, 3H), 2.17 (s, 3H), 1.35 (t, 3H).

Example 43

ETHYL 4-[N-(1'-AMINO-3'-PHENYLMALEIMIDO)]-2-TRIFLUOROMETHYLPRYRIMIDINE-5-CARBOXYLATE

The title compound was prepared as described in Example 20, but employing a solution of ethyl 4-hydrazino-2-trifluoromethylpyrimidine-5-carboxylate (0.09 g, 0.36 mmol) and 3-phenylmaleic anhydride (0.13 g, 0.72 mmol) resulting in a 69% yield (0.10 g); m.p. 179–180° C.

Example 44

ETHYL 4-[N-(1'-AMINO-3',4'-DIMETHYLMALEIMIDO)]-2-TRIFLUOROMETHYLPYRIMIDINE-5-CARBOXYLATE

The title compound was prepared as described in Example 20, but employing a solution of ethyl 4-hydrazino-2trifluoromethylpyrimidine-5-carboxylate (0.09 g, 0.36 mmol) and 3,4-dimethylmaleic anhydride (0.09 g, 0.72 mmol) resulting in a 89% yield (0.12 g); m.p. 116–117° C.

Example 45

ETHYL 2-HYDRAZINO-4-METHYLPYRIMIDINE-5-CARBOXYLATE

The title compound was prepared as described in Example 18, but employing a solution of ethyl 2-chloro-4-methylpyrimidine-5-carboxylate (0.08 g, 0.39 mmol) and hydrazine (0.06 g, 2.0 mmol) in THF (7.8 mL) resulting in a 93% yield (0.07 g); $^1H$ NMR ($CDCl_3$) δ 8.86 (s, 1H), 6.64 (bs, 1H), 4.33 (q, 2H), 2.70 (s, 3H), 1.38 (t, 3H).

Example 46

ETHYL 2-[N-(1'-AMINOCITRACONAMIDO)]-4-METHYLPYRIMIDINE-5-CARBOXYLATE

The title compound was prepared as described in Example 20, but employing a solution of ethyl 2-hydrazino-4-methylpyrimidine-5-carboxylate (0.07 g, 0.36 mmol) and citraconic anhydride (0.08 g, 0.72 mmol) resulting in a 52% yield (0.06 g); m.p. 49–50° C.

Example 47

ETHYL 2-HYDRAZINO-4-PENTAFLUOROETHYLPYRIMIDINE-5-CARBOXYLATE

The title compound was prepared as described in Example 18, but employing a solution of ethyl 2-chloro-4-pentafluoroethylpyrimidine-5-carboxylate (0.30 g, 0.99 mmol) and hydrazine (0.16 g, 5.0 mmol) in THF (20 mL) resulting in a 95% yield (0.28 g); $^1H$ NMR ($CDCl_3$) δ 8.86 (bs, 1H), 7.12 (bs, 1H), 4.37 (q, 2H), 1.72 (bs, 2H), 1.38 (t, 3H).

Example 48

ETHYL 2-[N-(1'-AMINOCITRACONAMIDO)]-4-PENTAFLUOROETHYLPYRIMIDINE-5-CARBOXYLATE

The title compound was prepared as described in Example 20, but employing a solution of ethyl 2-hydrazino-4-pentafluoroethylpyrimidine-5-carboxylate (0.28 g, 0.93 mmol) and citraconic anhydride (0.13 g, 1.1 mmol) resulting in a 68% yield (0.25 g); m.p. 73–74° C.

Example 49

ETHYL 2-HYDRAZINO-4-PHENYLPYRIMIDINE-5-CARBOXYLATE

The title compound was prepared as described in Example 18, but employing a solution of ethyl 2-chloro-4-phenylpyrimidine-5-carboxylate (0.09 g, 0.34 mmol) and hydrazine (0.06 g, 1.7 mmol) in THF resulting in a 91% yield (0.08 g); m.p. 74–75° C.

Example 50

ETHYL 2-[N-(1'-AMINOCITRACONAMIDO)]-4-PHENYLPYRIMIDINE-5-CARBOXYLATE

The title compound was prepared as described in Example 20, but employing a solution of ethyl 2-hydrazino-4-phenylpyrimidine-5-carboxylate (0.08 g, 0.31 mmol) and citraconic anhydride (0.04 g, 0.37 mmol) resulting in a 64% yield (0.07 g); m.p. 165–167° C.

Example 51

ETHYL 2-HYDRAZINO-4-BENZYLPYRIMIDINE-5-CARBOXYLATE

The title compound was prepared as described in Example 18, but employing a solution of ethyl 2-chloro-4-benzylpyrimidine-5-carboxylate (0.34 g, 1.2 mmol) and hydrazine (0.2 g, 6.1 mmol) in THF resulting in a 99% yield (0.33 g, oil); GC/MS, 272($M^+$).

Example 52

ETHYL 2-[N-(1'-AMINOCITRACONAMIDO)]-4-BENZYLPYRIMIDINE-5-CARBOXYLATE

The title compound was prepared as described in Example 20, but employing a solution of ethyl 2-hydrazino-4-benzylpyrimidine-5-carboxylate (0.34 g, 1.2 mmol) and citraconic anhydride (0.22 g, 2.0 mmol) resulting in a 37% yield (0.15 g) of the title compound; m.p. 34–36° C.

Example 53

METHYL 2-HYDROXY-4-(3'-PYRIDYL)PYRIMIDINE-5-CARBOXYLATE

The title compound was prepared as described in Example 5, but employing a solution of methyl ureidomethylene nicotinoyl acetate (8.4 g, 34 mmol) Na (1.0 g, 44 mmol) in EtOH (200 mL) resulting in a 52% yield (4.4 g); $^1$H NMR (DMSO-$d_6$) δ 8.59 (s, 1H), 8.51 (m, 2H), 7.72 (m, 1H), 7.36 (m, 1H), 3.51 (s, 3H).

Example 54

METYL 2-HLORO-4-(3'-PYRIDYL)PYRIMIDINE-5-CARBOXYLATE

The title compound was prepared as described in Example 7, but employing a solution of methyl 2-hydroxy-4-(3'-pyridyl)pyrimidine-5-carboxylate (4.42 g, 18 mmol) and POCl$_3$ (53.6 g, 350 mmol) resulting in a 25% yield (1.1 g); $^1$H NMR (DMSO-$d_6$) δ 9.11 (s, 1H), 8.77 (m, 2H), 8.03 (m, 1H), 7.45 (m, 1H), 3.85 (s, 3H).

Example 55

METHYL 2-HYDRAZINO-4-(3'-PYRIDYL)PYRIMIDINE-5-CARBOXYLATE

The title compound was prepared as described in Example 18, but employing a solution of methyl 2-chloro-4-(3'-pyridyl)pyrimidine-5-carboxylate (0.10 g, 0.42 mmol) and hydrazine (67 mg, 2.1 mmol) resulting in a 97% yield (0.10 g); $^1$H NMR (DMSO-$d_6$) δ 9.09 (s, 1H), 8.76 (d, 1H), 8.69 (d, 1H), 8.35 (bs, 1H), 7.89 (d, 1H), 7.42 (m, 1H), 3.76 (s, 2H), 2.19 (bs, 2H).

Example 56

METHYL 2-[N-(1'-AMINOCITRACONAMIDO)]-4-(3'-PYRIDYL)PYRIMIDINE-5-CARBOXYLATE

The title compound was prepared as described in Example 20, but employing a solution of methyl 2-hydrazino-4-(3'-pyridyl)pyrimidine-5-carboxylate (0.1 g, 0.39 mmol) and citraconic anhydride (0.04 g, 0.39 mmol) resulting in a 42% yield (0.06 g); m.p. 93–94° C.

Example 57

ETHYL 2-HYDROXY-4-BENZYLPYRIMIDINE-5-CARBOXYLATE

A solution of benzyl acetoacetate (7.0 g, 34 mmol) and N,N-dimethylformamide dimethyl acetal (4.0 g, 34 mmol) was stirred at room temperature for 0.25 h. The solution was concentrated and treated with urea (2.2 g, 37 mmol) and Na (1.2 g, 51 mmol) in EtOH (100 mL). The mixture was heated at reflux for 18 h, concentrated, acidified and purified by chromatography (SiO$_2$) to yield the desired product (2.6 g, 30%); m.p. 57–61° C.

Example 58

ETHYL 2-HLORO-4-BENZYLPYRIMIDINE-5-CARBOXYLATE

The title compound was prepared as described in Example 7, but employing a solution of ethyl 2-hydroxy-4-benzylpyrimidine-5-carboxylate (1.1 g, 4.3 mmol) and POCl$_3$ (16 g, 107 mmol) resulting in a 37% yield (0.44 g); $^1$H NMR (DMSO-$d_6$) δ 9.00 (s, 1H), 7.6–7.4 (m, 5H), 4.55 (s, 2H), 4.25 (q, 2H), 1.14 (t, 3H).

Example 59

DIETHYL UREIDOMETHYLENE OXALACETATE

A solution of diethyl oxalacetate (5.7 g, 30.4 mmol), triethyl orthoformate (8.8 g, 30 mmol) and urea (2.0 g, 30 mmol) was heated at reflux for 1.5 h. The product was filtered, washed with water and ether to give (3.5 g, 45%) of the title compound; $^1$H NMR (DMSO-$d_6$) δ 11.29 and 10.81 (dd, 1H), 8.6–7.4 (m, 3H), 4.2 (m, 4H), 1.24 (m, 6H).

Example 60

METHYL UREIDOMETHYLENE NICOTINOYL ACETATE

The title compound was prepared as described in Example 3, but employing a solution of methyl nicotinoyl acetate (10 g, 56 mmol), triethyl orthoformate (8.3 g, 56 mmol) and urea (3.4 g, 56 mmol) resulting in a 60% yield (8.4 g); $^1$H NMR (DMSO-$d_6$) δ 10.85 and 10.36 (dd, 1H), 8.8–7.2 (m, 7H), 3.58 (d, 3H).

Example 61

DIETHYL 2-HYDROXYPYRIMIDINE-4,5-DICARBOXYLATE

A solution of diethyl ureidomethylene oxalacetate (18.3 g, 71 mmol) in xylene (95 mL) was heated at reflux for 18 h. The reaction was cooled and the resulting solid was filtered. The solid was recrystallized from EtOAc to give the desired compound (8.2 g, 48%); $^1$H NMR (DMSO-$d_6$) δ 8.61 (s, 1H), 4.25 (m, 4H), 1.27 (m, 6H).

Example 62

DIETHYL 2-HLOROPYRIMIDINE-4,5-DICARBOXYLATE

The title compound was prepared as described in Example 7, but employing a solution of diethyl 2-hydroxypyrimidine-4,5-dicarboxylate (1.0 g, 4.2 mmol) and POCl$_3$ (7.7 g, 50 mmol) resulting in a 30% yield (0.32 g); $^1$H NMR (CDCl$_3$) δ 9.09 (d, 1H), 4.35 (m, 4H), 1.30 (m, 6H).

Example 63

DIETHYL 2-HYDRAZINOPYRIMIDINE-4,5-DICARBOXYLATE

The title compound was prepared as described in Example 18, but employing a solution of diethyl 2-chloropyrimidine-4,5-dicarboxylate (0.21 g, 0.83 mmol) and hydrazine (0.13 g, 4.2 mmol) in THF (10 mL) resulting in 96% yield (0.20 g); $^1$H NMR (CDCl$_3$) δ 8.93 (bs, 1H), 8.34 (bs, 1H), 4.40 (m, 4H), 4.18 (bs, 2H), 1.35 (m, 6H).

Example 64

DIETHYL 2-[N-(1'-AMINOCITRACONAMIDO)]PYRIMIDINE-4,5-DICARBOXYLATE

The title compound was prepared as described in Example 20, but employing a solution diethyl 2-hydrazinopyrimidine-4,5-dicarboxylate (0.20 g, 0.79 mmol) and citraconic anhydride (0.11 g, 0.95 mmol) resulting in a 77% yield (0.21 g); $^1$H NMR (CDCl$_3$) δ 8.94 (s, 1H), 8.88 (bs, 1H), 6.53 (s, 1H), 4.35 (m, 4H), 2.16 (s, 3H), 1.33 (m, 6H).

Example 65

ETHYL 2-[N-(1'-AMINO-3'-METHYLSUCCINIMIDO)]-4-TRIFLUOROMETHYLPYRIMIDINE-5-CARBOXYLATE

To a solution of ethyl 2-[N-(1'-amninocitraconamido)]-4-trifluoromethylpyrimidine-5-carboxylate (0.05 g, 0.15 mmol) in EtOH (20 ml) was added Pd/C (0.1 g). The reaction was stirred under an atmosphere of $H_2$ overnight. The mixture was filtered over celite and concentrated to give the title compound (0.047 g, 94% yield); $^1$H NMR (CDCl$_3$) δ 9.00 (s, 1H), 8.39 (s, 1H), 4.40 (q, 2H), 3.10 (m, 2H), 2.44 (m, 1H), 1.38 (m, 3H).

Example 66

METHYL 2-[N-(1'-AMINO-3'-METHYLSUCCINIMIDO)]-4-TRIFLUOROMETHYLPYRIMIDINE-5-CARBOXYLATE

The title compound was prepared as described in Example 65, but employing methyl 2-[N-(1'-aminocitraconamido)]-4-trifluoromethylpyrimidine-5-carboxylate (0.02 g, 0.06 mmol), resulting in a yield of 94% (0.019 g); m.p. 66–68° C.

Example 67

ETHYL 2-[N-(1'-AMINOCITRACONAMIDO)]-4-[2'-(5"-CHLOROTHIENYL]-PYRIMIDINE-5-CARBOXYLATE

A solution of 5-chlorothiophene-2-carboxylic acid (16.3 g, 0.1 mole) and carbonyl diimidazole (27.8 g, 0.17 mol) in THF (200 mL) was stirred 30 minutes. Bis(ethyl malonate) magnesium salt (14.4 g, 0.051 mol) was added and the mixture was refluxed for 7 hours, cooled to RT and concentrated. EtOAc (200 mL) and 6N HCl (50 mL) were added and the organic layer was separated, dried (MgSO$_4$), and concentrated. The ethyl 5-chloro-2-thiophenoylacetate (23 g, 0.1 mol) and N,N-dimethylformamide dimethyl acetal (12 g, 0.1 mol) were stirred for 1 hour and concentrated. To this was added, a solution of NaOEt previously prepared using sodium in EtOH [Na (2.3 g, 0.1 mol) dissolved in 500 mL EtOH] and S-methyl isothiouronium sulfate (13.9 g, 0.05 mol) that was allowed to stir for 30 minutes. The mixture was refluxed for 4 hours, cooled to RT, concentrated, dissolved in EtOAC (500 mL), washed with 4N HCl (2×50 mL), dried (MgSO$_4$) and the solvent replaced with CH$_2$Cl$_2$ (300 mL). The solution was cooled to 0° C., mCPBA (51 g, 0.3 mol) was slowly added, and the solution was allowed to reach RT. After stirring for 2 hours, the solution was quenched by slowly pouring into a cold satd. NaHSO$_3$ solution (100 mL). The organic layer was then washed with satd. NaHCO$_3$ (100 mL), dried (MgSO$_4$), and concentrated. From this, the title compound was prepared as described in Example 20, but employing the ethyl 2-hydrazino-4-[2'-(5'-chlorothiophene)]pyrimidine-5-carboxyl (3.0 g, 0.017 mol) {prepared according to the procedure of Example 19, but employing ethyl 2-mesyl-4-[2'-(5'-chlorothiophene)]pyrimidine-5-carboxylate described above}, resulting in a yield of 38% (1.3 g); m.p. 137–138° C.

Example 68

ETHYL 2-[N-(1'-AMINOCITRACONAMIDO)-N-METHYL]-4-[2'-(5"-HLOROTHIENYL]PYRIMIDINE-5-CARBOXYLATE

The title compound was prepared as described in Example 67 from 4-[2'(5'-chlorothiophene)-2-hydrazino-5-pyrimidine carboxylate (0.5 g, 1.7 mmol), but employing methyl hydrazine (0.35 g, 7.5 mmol) where hydrazine was used, resulting in a yield of 48% (0.32 g); GC/MS calcd for $C_{17}H_{15}N_4O_4SCl$ (M$^+$) 406, found 406.

Example 69

ETHYL 2-[N-(1'-AMINO-4'-METHYLPHTHALIMIDO)]-4-TRIFLUOROMETHYLPRYMIDINE-5-CARBOXYLATE

The title compound was prepared as described in Example 20, employing ethyl 2-hydrazino-4-trifluoromethylpyrimidine-5-carboxylate (0.20 g, 0.8 mmol) and 4-methylphthalic anhydride (0.26 g, 1.6 mmol) where citraconic anhydride was used, resulting in a yield of 29% (0.09 g); m.p. 50–51° C.

Example 70

ETHYL 2-[N-(1'-AMINO-4',5'-DICHLOROPHTHALIMIDO)]-4-TRIFLUOROMETHYLPYRIMIDINE-5-CARBOXYLATE

The title compound was prepared as described in Example 20, employing ethyl 2-hydrazino-4-trifluoromethylpyrimidine-5-carboxylate (0.20 g, 0.8 mmol) and 4,5-dichlorophthalic anhydride (0.35 g, 1.6 mmol) where citraconic anhydride was used, resulting in a yield of 61% (0.22 g); m.p. 142–144° C.

Example 71

ETHYL 2-[N-(1'-CITRACONAMIDO)]-PYRIMIDINE-5-CARBOXYLATE

The title compound was prepared by (a) treating 2-chloropyrimidine-5-carbonylchloride (Example 13, 110 mg, 0.62 mmol) with ethanol (200 mg, 4.4 mmol in 1 mL of ethyl acetate) to provide 60% of ethyl 2-chloropyrimidine-5-carboxylate, (b) reaction of ethyl 2-chloropyrimidine-5-carboxylate (70 mg, 0.37 mmol) with hydrazine (100 mg, 3 mmol) to afford 44% of ethyl 4-hydrazinopyrimidine-5-carboxylate as in Example 19, (c) reaction of ethyl 4-hydrazinopyrimidine-5-carboxylate (0.36 g, 2.0 mmol) with citraconic anhydride (0.34 g, 3.0 mmol) in analogy to Example 21 to afford 10% (0.05 g) of the title compound; m.p. 95–98° C.

Example 72

5-BENZOYL-4-ETHYL-2-METHYLTHIOPYRIMIDINE

The title compound was prepared by (a) reaction of ethyl propionylacetate (19.4 g, 0.13 mol) and N,N-dimethylformamide dimethyl acetal (16.0 g, 0.13 mol) in analogy to Example 67, (b) reaction with NaOEt (0.18 mol) and S-methyl isothouronium sulfate (18.7 g, 0.067 mol) also described for Example 67, (c) hydrolysis of the ethyl 4-ethyl-2-methylthiopyrimidine-5-carboxylate (18.0 g, 0.08 mmol) with NaOH (12.7 g, 0.32 mol) in H$_2$O (200 mL) as described in Example 67, (d) reaction of the 4-ethyl-2-methylthiopyrimidine-5-carboxylic acid (0.50 g, 2.5 mmol) and oxalyl chloride (0.32 g, 2.5 mmol) as described in Example 11, and (e) reaction of the 4-ethyl-2-methylthiopyrimidine-5-carbonyl chloride (0.50 g, 2.3 mmol) and phenyl magnesium bromide as described for Example 23, resulting in a yield of 22% (0.14 g) from the 4-ethyl-2-methylthiopyrimidine-5-carboxylic acid;); $^1$H NMR (CDCl$_3$) δ 9.18 (s, 1H), 7.80 (d, 2H), 7.62 (t, 1H), 7.50 (t, 2H), 2.81 (q, 2H), 2.61 (s, 3H), 1.22 (t, 3H).

Example 73

ETHYL 2-[N-(1'-AMINOCITRACONAMIDO)-N-METHYL]-4-ETHYLPRYMIDINE-5-CARBOXYLATE

The title compound was prepared as described in Example 42, but employing ethyl 2-[N-(1'-aminocitraconamido)]-4-ethylpyrimidine-5-carboxylate (0.05 g, 0.16 mmol), resulting in a yield of 76% (0.04 g); $^1$H NMR (CDCl$_3$) δ 8.80 (d, 1H), 6.46 (s, 1H), 4.30 (q, 2H), 3.58 (s, 3H), 3.18 (m, 2H), 2.16 (s, 3H), 1.33 (m, 6H).

Example 74

ETHYL 2-[N-ACETYL-N-(1'-AMINOCITRACONAMIDO)]-4-PROPYLPYRIMIDINE-5-CARBOXYLATE

Ethyl 2-[N-(1'-aminocitraconamido)]-4-propylpyrimidine-5-carboxylate (0.060 g, 0.19 mmole) and 1.5 mL of an acetic anhydride and pyridine (1:1 molar) solution were stirred overnight. Concentration and chromatography (SiO$_2$, hexanes/EtOAc, 3:2) provided the title compound (0.03 g, 44% yield); $^1$H NMR (CDCl$_3$) δ 9.0 (s, 1H), 6.5 (s, 1H), 4.4 (q, 2H), 3.1 (t, 2H), 2.82 (s, 3H), 2.19 (s, 3H), 1.7 (m, 2H), 1.39 (t, 3H), 0.99 (t, 3H).

Example 75

ETHYL 2-[N-ACETYL-N-(1'-AMINOCITRACONAMIDO)]-4-TRIFLUOROMETHYLPYRIMIDINE-5-CARBOXYLATE

The title compound was prepared as described in Example 74, but employing ethyl 2-[N-(1'-aminocitraconamido)]-4-trifluoromethylpyrimidine-5-carboxylate (0.14 g, 0.4 mmol), resulting in a yield of 67% (0.11 g); $^1$H NMR (CDCl$_3$) δ 9.14 (s, 1H), 6.55 (s, 1H), 4.45 (q, 2H), 2.83 (s, 3H), 2.20 (s, 3H), 1.39 (t, 3H).

Example 76

METHYL 2-HYDRAZINO-4-PENTAFLUOROETHYLPYRIMIDINE-5-CARBOXYLATE

The title compound was prepared according to the procedure of Example 47 but employing a solution of methyl 2-chloro-4-pentafluoroethylpyrimidine-5-carboxylate (0.55 g, 1.9 mmol; itself prepared by a reaction of methanol with 2-chloro-4-pentafluoroethylpyrimidine-5-carbonyl chloride (see Example 17)) and hydrazine (0.3 g, 9.4 mmol), resulting in a yield of 99% (0.54 g); $^1$HNMR (CDCl$_3$) δ 8.87 (s, 1H), 7.09 (s, 1H), 3.92 (s, 3H), 1.7 (s, 2H).

Example 77

METHYL 2-[N-(1'-AMINOCITRACONAMIDO)]-4-PENTAFLUOROETHYLPYRIMIDINE-5-CARBOXYLATE

The title compound was prepared according to the procedure of Example 20 but employing 2-hydrazino-4-pentafluoroethylpyrimidine-5-carboxylate (0.54 g, 1.9 mmol) and citraconic anhydride (0.25 g, 2.3 mmol), resulting in a yield of 98% 0.71 g); m.p. 94–95° C.

Example 78

METHYL 2-[N-(1'-AMINOCITRACONAMIDO)]-N-METHYL]-4-PENTAFLUOROETHYLPYRIMIDINE-5-CARBOXYLATE

The title compound was prepared according to the procedure of Example 73 but employing methyl 2-[N-(1'-aminocitraconamido)]-4-pentafluoroethylpyrimidine-5-carboxylate (0.05 g, 0.13 mmol), a base and methyl iodide (0.04 g, 0.26 mmol); $^1$HNMR (CDCl$_3$) δ 9.02 (s, 1H), 8.79 (s, 1H), 6.49 (m, 1H), 3.92 (s, 3H), 3.59 (d, 3H), 2.16 (d, 3H).

Example 79 t-BUTYL 2-[N-(1'-AMINOCITRACONAMIDO)]-4-TRIFLUOROMETHYLPYRIMIDINE-5-CARBOXYLATE

The title compound was prepared from t-butyl 2-hydrazino-4-trifluoromethylpyidine-5-carboxylate (0.88 g, 3.2 mmol) (prepared as described for Example 19, but employing t-butyl 2-chloro-4-trifluoromethylpyrimidine-5-carboxylate) as described in Example 20, resulting in a yield of 10% (0.12 g); $^1$H NMR (CDCl$_3$) δ 8.84 (s, 1H), 7.50 (s, 1H), 6.53 (s, 1H), 2.20 (s, 3H), 1.55 (s, 9H).

Example 80

METHYL 2-[N-(1'-AMINOCITRACONAMIDO)]-4-TRIFLUOROMETHYLPYRIMIDINE-5-CARBOXYLATE

The title compound was prepared from methyl 2-hydrazino-4-trifluoromethylpyrimidine-5-carboxylate (0.01 g, 0.42 mmol) (prepared as described for Example 19, but employing methyl 2-chloro-4-trifluoromethylpyrimidine-5-carboxylate) as described in Example 20, resulting in a yield of 69% (0.096 g); m.p. 118–120° C.

Example 81

METHYL 2-[N-(1'-AMINOCITRACONAMIDO)-N-METHYL]-4-TRIFLUOROMETHYLPYRIMIDINE-5-CARBOXYLATE

The title compound was prepared from methyl 2-[N-(1-aminocitraconamido)]-4-trifluoromethylpyrimidine-5-carboxylate (0.20 g, 6.1 mmol) as described in Example 42, resulting in a yield of 10% (0.02 g); $^1$H NMR (CDCl$_3$) δ 9.05 (s, 1H), 6.49 (s, 1H), 3.91 (s, 3H), 3.62 (s, 3H), 2.18 (s, 3H).

Example 82

METHYL 2-HYDRAZINO-4-(2'-THIENYL)PYRIMIDINE-5-CARBOXYLATE

A solution of ethyl 2-hydroxy-4-(2'-thienyl)pyrimidine-5-carboxylate (2.7 g, 10.8 mmol) and NaOH (1.3 g, 32.4 mmol) in H$_2$O (25 mL) was stirred overnight then acidified to pH<2 using concentrated HCl. The precipitate was collected, dried under vacuum, and POCl$_3$ (16.5 g, 108 mmol) was added. To this was added diethylaniline (1.6 g, 10.8 mmol), and the mixture was refluxed for 30 minutes. The solution was cooled, concentrated, poured over ice and extracted with ether (200 mL). The 2-chloro-4-(2'-thienyl)pyrimidine-5-carboxylic acid was then dissolved in CH$_2$Cl$_2$ (30 mL), treated with oxalyl chloride (5.4 g, 42.7 mmol) and DMF (2 drops), and allowed to stir overnight. The solution was then concentrated, dissolved in MeOH (10 mL) and concentrated after stirring 10 minutes. The title compound was prepared from the crude methyl 2-chloro-4-(2'-thienyl)pyrimidine-5-carboxylate as described in Example 19, resulting in a overall yield of 6% (0.16 g); GC/MS calcd for C$_{10}$H$_{10}$N$_4$O$_2$S (M$^+$) 250, found 250.

Example 83

METHYL 2-[N-(1'-AMINOCITRACONAMIDO)]-4-(2'-THIENYL)PYRIMIDINE-5-CARBOXYLATE

The title compound was prepared from methyl 2-hydrazino-4-(2'-thienyl)pyrimidine-5-carboxylate (0.16 g, 0.64 mmol) according to the procedure of Example 20, resulting in a yield of 90% (0.20 g); m.p. 112–113° C.

Example 84

ETHYL 2-[N-(1'-AMINOCITRACONAMIDO-N-BENZYL)]-4-TRIFLUOROMETHYLPYRIMIDINE-5-CARBOXYLATE

The title compound was prepared from ethyl 2-hydrazino-1'-benzyl)-4-trifluoromethylpyrimidine-5-carboxylate (0.2 g, 0.78 mmol) (prepared according to the procedure of Example 19 but employing benzylhydrazine) as described in Example 20, resulting in a yield of 12% (0.05 g); $^1$H NMR (CDCl$_3$) δ 9.08 (d, 1H), 7.3 (m, 5H), 6.39 (s, 1H), 5.21 (m, 2H), 4.37 (m, 2H), 2.09 (s, 3H), 1.37 (m, 3H).

Example 85

ETHYL 2-[N-(1'-AMINOCITRACONAMIDO-N-METHYL)]-4-(2'-THIENYL)PYRIMIDINE-5-CARBOXYLATE

The title compound was prepared from ethyl 2-[N-(1'-aminocitraconamido)]-4-(2'-thienyl)pyrimidine-5-carboxylate (0.05 g, 0.14 mmol) according to the procedure of Example 42, resulting in a yield of 19% (0.01 g); $^1$H NMR (CDCl$_3$) δ 8.83 (d, 1H), 7.78 (m, 1H), 7.41 (m, 1H), 7.10 (m, 1H), 6.47 (d, 1H), 4.34 (m, 2H), 3.61 (s, 3H), 2.20 (d, 3H), 1.33 (m, 3H).

Example 86

2-[N-(1'-AMINOCITRACONAMIDO)]-4-TRIFLUOROMETHYLPYRIMIDINE-5-CARBOXYLIC ACID

A solution of t-butyl 2-[N-(1'-aminocitraconamido)]-4-trifluoromethylpyrimidine-5-carboxylate (0.20 g, 0.5 mmol) in concentrated formic acid (8 mL) was refluxed for one hour, cooled, diluted with H$_2$O (10 mL), extracted with EtOAc (2×20 mL), dried (MgSO$_4$) and concentrated. The solid was washed with CH$_2$Cl$_2$ (2×20 mL) and dried under vacuum to give the title compound in 60% yield (0.10 g); m.p. 107–109° C.

Example 87

5-BENZOYL 2-[N-(1'-AMINOCITRACONAMIDO)]-4-TRIFLUOROMETHYLPYRIMIDINE

The title compound was prepared from 5-benzoyl-2-hydrazino-4-trifluoromethylpyrimidine (0.15 g, 0.53 mmol) (prepared as described for Example 19, but employing 5-benzoyl-2-mesyl-4-trifluoromethylpyrimidine) as described in Example 20, resulting in a yield of 6% (0.015 g); $^1$H NMR (CDCl$_3$) δ 8.5 (s,1H), 7.8 (m,2H), 7.65 (m,1H), 7.5 (m,2H), 6.5 (s,1H), 3.45 (s,1H), 2.2 (s,3H).

Example 88

ETHYL 2-[N-(1'-AMINOCITRACONAMIDO)]-4-(3'-THIENYL)PYRIMIDINE-5-CARBOXYLATE

The title compound was prepared from ethyl 2-hydrazino-4-(3'-thienyl)pyrimidine-5-carboxylate (0.22 g, 0.88 mmol) (prepared in the same manner as Example 35) as described in Example 20, resulting in a yield of 40% (0.11 g); m.p. 47–48° C.

Example 89

ETHYL 2-[N-(1'-AMINOCITRACONAMIDO-N-METHYL)]-4-(3-THIENYL)PYRIMIDINE-5-CARBOXYLATE

The title compound was prepared from ethyl 2-[N-(1'-aminocitraconamido)]-4-(3'-thienyl)pyrimidine-5-carboxylate (0.05 g, 0.14 mmol) as described in Example 42, resulting in a yield of 19% (0.01 g); 39–41° C.

Example 90

ETHYL 2-[N-(1'-AMINOCITRACONAMIDO)]-4-[2'-(5'-METHYLTHIENYL)]PYRIMIDINE-5-CARBOXYLATE

The title compound was prepared from ethyl 2-hydrazino-4-[2'-(5'-methylthienyl)]pyrimidine-5-carboxylate (0.22 g, 0.88 mmol) (prepared in the same manner as Example 67) as described for Example 20, resulting in a yield of 40% (0.11 g); m.p. 138–139° C.

Example 91

ETHYL 2-[N-(1'-AMINOCITRACONAMIDO)]-4-(2'-FURANYL)PYRIMIDINE-5-CARBOXYLATE

The title compound was prepared by (a) reaction of ethyl 2'-furanoylacetate (10 g, 0.055 mol) with N,N-dimethylformamide dimethyl acetal (7.3 g, 0.055 mol) as described for Example 67, (b) subsequent reaction with a solution NaOEt (0.058 mol) and S-methyl isothouronium sulfate (7.7 g, 0.028 mol) also described for Example 67, (c) oxidation with mCPBA (9.8 g, 0.057 mol) also described for Example 67, (d) reaction with hydrazine (1.5 mL, 0.05 mol) as described for Example 19, and (e) reaction with citraconic anhydride (4 mL, 0.05 mol) as described for Example 20, resulting in an overall yield of 1% (0.18 g); m.p. 38—40° C.

Example 92

ETHYL 2-[N-(1'-AMINOCITRACONAMIDO-N-METHYL)]-4-[2'-(5'-METHYLTHIENYL)]PYRIMIDINE-5-CARBOXYLATE

The title compound was prepared from ethyl 2-(1'-methylhydrazino)-4-[2'-(5'-methylthienyl)]pyrimidine-5-carboxylate (3.0 g, 10.0 mmol) (prepared in the same manner as Example 67 employing methyl hydrazine) as described in Example 20, resulting in a yield of 40% (1.6 g); $^1$H NMR (CDCl$_3$) δ 8.71 (d,1H), 7.7 (d,1H), 6.74 (d,1H), 6.5 (d,1H), 4.33 (q,2H), 3.6 (s,3H), 2.5 (d,3H), 2.2 (d,3H), 1.32 (t,3H).

Example 93

ETHYL 2-[N-(1'-AMINOCITRACONAMIDO)]-4-(2'-THIANAPHTHYL)PYRIMIDINE-5-CARBOXYLATE

The title compound was prepared by (a) reaction of ethyl 2'-benzothienoylacetate (24.8 g, 0.1 mol) with N,N-dimethylformamide dimethyl acetal (7.3 g, 0.055 mol) as described for Example 67, (b) subsequent reaction with a solution of NaOEt (0.12 mol) and S-methyl isothouronium sulfate (13.9 g, 0.05 mol) also described for Example 67, (c) oxidation with mCPBA (8.5 g, 0.05 mol) also described for Example 67, (d) reaction with hydrazine (1.5 mL, 0.05 mol) as described for Example 19, and (e) reaction with citraconic anhydride (4 mL, 0.05 mol) as described for Example 20, resulting in an overall yield of 0.1% (0.05 g); m.p. 165–166° C.

Example 94

METHYL 2-[N-(1'-AMINOCITRACONAMIDO-N-ETHYL)]-4-TRIFLUOROMETHYLPYRIMIDINE-5-CARBOXYLATE

The title compound was prepared from methyl 2-[N-(1'-aminocitraconamido)]-4-trifluoromethylpyrimidine-5-carboxylate (0.20 g, 0.61 mmol) as described for Example 42, but employing ethyliodide, resulting in a yield of 18% (0.04 g); $^1$H NMR (CDCl$_3$) δ 9.01 (d, 1H), 6.48 (s, 1H), 4.05 (q, 2H), 3.87 (s, 3H), 2.14 (s, 3H), 1.27 (t, 3H).

Example 95

ETHYL 2-[N-(1'-AMINOCITRACONAMIDO-N-BUTANOYL)]-4-TRIFLUOROMETHYLPYRIMIDINE-5-CARBOXYLATE

The title compound was prepared from ethyl 2-[N-(1'-aminocitraconamido)]-4-trifluoromethylpyrimidine-5- carboxylate (0.10 g, 0.29 mmol) as described for Example 74, but employing butyric anhydride, resulting in a yield of 23% (0.03 g); $^1$H NMR (CDCl$_3$) δ 9.13 (s, 1H), 6.54 (s, 1H), 4.42 (q, 2H), 3.17 (t, 2H), 2.18 (s, 3H), 1.77 (q, 2H), 1.36 (t, 3H), 1.01 (t, 3H).

Example 96

ETHYL 2-[N-(1'-AMINOCITRACONAMIDO)-N-(N'-METHYLCARBOXAMIDYL)]-4-TRIFLUOROMETHYLPYRIMIDINE-5-CARBOXYLATE

Ethyl 2-[N-(1'-aminocitraconamido)]-4-trifluoromethylpyrimi-dine-5-carboxylate (0.05 g, 0.15 mmol) and methylisocyanate (0.3 mL) were heated to 60° C. for 3 minutes and allowed to cool to RT. After 30 minutes, the residual isocyanate was removed under vacuum, and the solid was washed with hexanes to provide the title compound in a 70% yield (0.03 g); m.p. 132–134° C.

Example 97

ETHYL 2-[N-(1'-AMINOCITRACONAMIDO)-N-(1-OXO-2"-PHENYLETHYL]-4-TRIFLUOROMETHYLPYRIMIDINE-5-CARBOXYLATE

A solution of ethyl 2-[N-(1'-aminocitraconamido)]-4-trifluoromethylpyrimidine-5-carboxylate (0.04 g, 0.12 mmol), phenylacetylchloride (0.08 mL, 0.6 mmol) and pyridine (0.05 mL, 0.6 mmol), in CH$_2$Cl$_2$ (15 mL) was stirred 1.5 hours, washed with H$_2$O, dried (MgSO$_4$), concentrated and chromatographed (SiO$_2$, hexanes/EtOAc, 2:1) to give the title compound in 42% yield (0.021 g); $^1$H NMR (CDCl$_3$) δ 9.11 (s, 1H), 7.27 (m, 5H), 6.53 (s, 1H), 4.46 (s, 2H), 4.42 (q, 2H), 2.17 (s, 3H), 1.37 (t, 3H).

Example 98

ETHYL 2-[N-(1'-AMINOCITRACONAMIDO)]-4-METHOXYMETHYL PYRIMIDINE-5-CARBOXYLATE

The title compound was prepared by (a) reaction of ethyl methoxyketoacetate (10.5 g, 0.07 mol) with triethyl orthoformate (9.7 g, 0.07 mol) and urea (3.9 g, 0.07 mol) as described for Example 3, (b) reaction with NaOEt (0.02 mol) as described for Example 5, (c) reaction with POCl$_3$ (6.5 mL, 0.07 mol) as described for Example 7, (d) reaction with hydrazine (2 mL, 0.07 mol) as described for Example 19, and (e) reaction with citraconic anhydride (6 mL, 0.07 mol) as described for Example 20, resulting in an overall yield of 8% (1.8 g); $^1$H NMR (CDCl$_3$) δ 8.87 (s, 1H), 8.2 (s, 1H), 6.5 (s, 1H), 4.87 (s, 2H), 4.35 (q, 2H), 3.47 (s, 3H), 2.18 (s, 3H), 1.35 (t, 3H).

Example 99

ETHYL 2-[N-(1'-AMINOCITRACONAMIDO)-N-(ETHOXYCARBONYL)]-4-TRIFLUOROMETHYLPYRIMIDINE-5-CARBOXYLATE

The title compound was prepared from ethyl 2-[N-(1'-aminocitraconamido)]-4-trifluoromethylpyrimidine-5-carboxylate (0.06 g, 0.19 mmol) as described for Example 97, but employing ethyl chloroformate, resulting in a yield of 71% (0.055 g); $^1$H NMR (CDCl$_3$) δ 9.13 (s, 1H), 6.54 (s, 1H), 4.39 (m, 4H), 2.18 (s, 3H), 1.31 (m, 6H).

Example 100

ETHYL 2-[N-(1'-AMINOCITRACONAMIDO)-N-BENZOYL]-4-TRIFLUOROMETHYLPYRIMIDINE-5-CARBOXYLATE

The title compound was prepared from ethyl 2-[N-(1'-aminocitraconamido)]-4-trifluoromethylpyrimidine-5-carboxylate (0.09 g, 0.26 mmol) as described for Example 97, but employing benzoyl chloride, resulting in a yield of 69% (0.08 g); $^1$H NMR (CDCl$_3$) δ 8.99 (s, 1H), 7.72 (d, 2H), 7.52 (dd, 1H), 7.41 (dd, 2H), 6.55 (s, 1H), 4.39 (q, 2H), 2.19 (s, 3H), 1.35 (t, 3H).

Example 101

5-BENZOYL 2-[N-(1'-AMINOCITRACONAMIDO)]-4-ETHYLPYRIMIDINE

The title compound was prepared by (a) reaction of 5-benzoyl-4-ethyl-2-methylthiopyrimidine (0.14 g, 0.54 mmol) and mCPBA (0.28 g, 1.6 mmol) as described for Example 67, (b) reaction with hydrazine (0.09 g, 2.7 mmol) as described for Example 19, and (c) reaction with citraconic anhydride as described for Example 20, resulting in a overall yield of 25% (0.046 g); m.p. 49–50° C.

Example 102

5-BENZOYL 2-[N-(1'-AMINOCITRACONAMIDO)-N-METHYL]-4-ETHYLPYRIMIDINE

The title compound was prepared as described for Example 42, but employing 2-[N-(1'-aminocitraconamido)]-5-benzoyl-4-ethylpyrimidine (0.06 g, 0.18 mmol), resulting in a yield of 40% (0.025 g); $^1$H NMR (CDCl$_3$) δ 8.41 (d, 1H), 7.78 (d, 2H), 7.60 (dd, 1H), 7.44 (dd, 2H), 6.43 (s, 1H), 3.61 (s, 3H), 2.68 (m 2H), 2.19 (s, 3H), 1.2 (m 3H).

Example 103

ETHYL-2-[N-(1'-AMINOCITRACONAMIDO)-N-METHYL]-4-PENTAFLUOROETHYLPYRIMIDINE-5-CARBOXYLATE

The title compound was prepared according to the procedure of Example 78 but employing ethyl-2-[N-(1'-aminocitraconamide)]-4-pentafluoroethylpyrimidine-5-carboxylate (0.1 g, 0.3 mmol) and methyl iodide (0.07 g, 0.5 mmol) under basic conditions, resulting in a yield of 47% (0.05 g); $^1$HNMR (CDCl$_3$) δ 9.01 (s, 1H), 8.80 (s, 1H), 6.49 (m, 1H), 4.39 (q, 2H), 3.62 (s, 3H), 2.18 (d, 3H), 1.36 (t, 3H).

Example 104

ETHYL 2-[N-(1'-AMINOCITRACONAMIDO)]-4-(2'-THIANAPHTHYL)PYRIMIDINE-5-CARBOXYLATE

The title compound was prepared from ethyl 2-mesyl-4-(2'-thianaphthyl)pyrimidine-5-carboxylate (2.0 g, 5.5 mmol) as described in Example 93, but employing methyl hydrazine (0.9 mL, 16.5 mmol) where hydrazine was used, this followed by reaction with citraconic anhydride (1.5 mL, 16.5 mmol) also in analogy to Example 93; resulting in a yield of 69% (1.6 g); $^1$H NMR (CDCl$_3$) δ 8.8 (d, 1H), 8.15 (d, 1H), 7.8 (m, 2H), 7.3 (m, 2H), 6.6 (d, 1H), 4.37 (q, 2H), 3.65 (d, 3H), 2.17 (s, 3H), 1.34 (t, 3H).

Example 105

ETHYL 2-[N-(1'-AMINOCITRACONAMIDO)]-4-(2'-THIAZOLYL)PYRIMIDINE-5-CARBOXYLATE

2-Bromothiazole (8.25 g, 0.05 moles) in anhydrous ether (60 mL) is added dropwise to a solution of nBuLi (34 mL, 1.5M solution, 0.051 mmol) in anhydrous ether (60 mL) cooled to −78° C. and stirred for 30 minutes. Carbon dioxide is bubbled into the solution and after saturation is achieved, the reaction mixture is poured over dry-ice. H$_2$O (10 mL) is added and the mixture basified to pH=9 with NaOH (1N). The aqueous layer is acidified with concentrated HCl to pH <3 then extracted into ether, dried (MgSO$_4$) and concentrated to provide the thiazole-2-carboxylic acid in 57% yield (3.2 g); $^1$H NMR (MeOD) δ 8.00 (d, 1H); 7.94 (d, 1H). The title compound was then prepared by (a) reaction of thiazole-2-carboxylic acid (3.7 g, 29.0 mmol) and bis(ethyl malonate)magnesium salt (4.3 g, 15.0 mmol) as described in Example 67, (b) reaction of 2-thiazolylacetate (2.5 g, 12.8 mmol) and N,N-dimethylformamide dimethyl acetal (2.42 g, 12.8 mmol) as described for Example 67, (c) reaction with NaOEt (13.8 mol) and S-methyl isothouronium sulfate (1.78 g, 6.4 mol) also described for Example 67, (d) oxidation with mCPBA (6.1 g, 35.0 mmol) also described for Example 67, (e) reaction of ethyl 2-mesyl-4-(2'-thiazolyl)pyrimidine-5-carboxylate (1.08 g, 3.45 mmol) with hydrazine (0.33 mL, 10.3 mmol) as described for Example 19, and (f) reaction with citraconic anhydride (0.31 mL, 3.5 mmol) described for Example 20, resulting in an overall yield of 8% (0.10 g) from ethyl 2-mesyl-4-(2'-thiazolyl)pyrimidine-5-carboxylate; m.p 42–44° C.

Example 106

ETHYL 2-[N-(1'-AMINOCITRACONAMIDO)-N-METHYL]-4-(2'-THIAZOLYL)PYRIMIDINE-5-CARBOXYLATE

The title compound was prepared as described in Example 20, but employing ethyl 2-(1'-methylhydrazino)-4-(2'-thiazolyl)pyrimidine-5-carboxylate (0.96 g, 3.4 mmol) (prepared according to the procedure of Example 19 but employing ethyl 2-mesyl-4-(2'-thiazolyl)pyrimidine-5-carboxylate and methyl hydrazine where hydrazine was used), resulting in a yield of 50% (0.64 g); $^1$H NMR δ 8.69 (bs, 1H); 7.92 (d, 1H); 7.50 (d, 1H); 6.50 (d, 1H); 4.35 (q, 2H); 3.62 (s, 3H); 2.2 (s, 3H); 1.27 (t, 3H).

Example 107

5-BUTANOYL 2-[N-(1'-AMINOCITRACONAMIDO-N-METHYL)]-4-ETHYLPYRIMIDINE

The title compound was prepared as described for Example 101, but employing 5-butanoyl-4-ethyl-2-methylthiopyrimidine (1.16 g, 5.2 mmol) (prepared as described for Example 72) where 5-benzoyl-4-ethyl-2-methylthiopyrimidine was used, resulting in an overall yield of 15% (0.24 g); $^1$H NMR δ 8.80 (d, 1H), 6.42 (d, 1H), 3.60 (s, 3H), 2.65 (m ,4H), 2.20 (s, 3H), 1.65 (m, 3H), 1.23 (m, 2H), 0.99 (m, 3H).

Example 108

ETHYL 2-[N-(1'-AMINOCITRACONAMIDO)]-4-CYCLOPROPYLPYRIMIDINE-5-CARBOXYLATE

The title compound was prepared as described for Example 67, but employing cyclopropanecarboxylic acid (5.5 g, 63.9 mmol) where 5-chlorothiophene-2-carboxylic acid was used, resulting in an overall yield of 0.8% (0.09 g); m.p. 76–78° C.

Example 109

ETHYL 2-[N-(1'-AMINOCITRACONAMIDO-N-METHYL)]-4-CYCLOPROPYLPYRIMIDINE-5-CARBOXYLATE

The title compound was prepared as described for Example 108 from cyclopropanecarboxylic acid (5.5 g, 63.9 mmol), but employing methyl hydrazine where hydrazine was used, resulting in an overall yield of 0.3% (0.062 g); m.p. 53–55° C.

Example 110

4-ETHYL-5-(HYDROXYMETHYL)-2-METHYLTHIOPYRIMIDINE

To a solution of ethyl 4-ethyl-2-methylthiopyrimidine-5-carboxylic acid (2.0 g, 10.1 mmol) (prepared as described in steps a–c of Example 72) and N-methyl morpholine (1.16 mL, 10.6 mmol) in dimethyl glycol (50 mL) at 0° C. was added isobutylchloroformate (1.38 mL, 10.6 mmol). The mixture was stirred 10 minutes, filtered, and cooled to 0° C. A solution of NaBH$_4$ (0.40 g, 10.6 mmol) in H$_2$O (10 mL) was added to the filtrate and the mixture was stirred for 10 minutes. H$_2$O (10 mL) was added and the mixture was extracted with EtOAc (100 mL),washed with brine (20 mL), and concentrated to provide the title compound in 56% yield (1.04 g); GC/MS calcd for C$_8$H$_{12}$N$_2$OS (M$^+$) 184, found 184.

Example 111

2-[N-(1'-AMINOCITRACONAMIDO)-N-METHYL]-4-ETHYL-5-(HYDROXYMETHYL)PYRIMIDINE

A solution of 5-hydroxymethyl-4-ethyl-2-methylthiopyrimidine (0.50 g, 2.72 mmol), t-butyldimethylsilylchloride (0.49 g, 3.26 mmol), and imidazole (0.20 g, 2.99 mmol) in DMF (5 mL) was stirred overnight and concentrated to give of 5-t-butyldimethylsiloxymethyl-4-ethyl-2-methylthiopyrimidine in a 94% yield (0.76 g); GC/MS calcd for C$_{14}$H$_{26}$N$_2$OSSi (M$^+$) 299, found 299. The title compound was then prepared by (a) oxidation of 5-t-butyldimethylsiloxymethyl-4-ethyl-2-methylthiopyrimidine (0.30 g, 1.0 mmol) with mCPBA (0.35 g, 2.0 mmol) as described for Example 67, (b) reaction with methyl hydrazine (0.16 mL, 3.0 mmol) followed by citraconic anhydride (0.11 g, 1.0 mmol) also described in Example 67; (c) reaction of 2-[N-(1'-aminocitraconamido)]-5-t-butyldimethylsiloxymethyl-4-ethylpyrimidine; (0.08 g, 0.21 mmol) and concentrated HCl (0.5 mL) in EtOH (20 mL) for 1 hour, concentration and chromatography (Hexanes/EtOAc, 2:1) to provide the title compound in 76% yield (0.043 g) from 2-[N-(1'-aminocitraconamido)]-5-t-butyldimethylsiloxymethyl-4-ethylpyrimidine; m.p. 108–110° C.

Example 112

2-[N-(1'-AMINOCITRACONAMIDO)-N-METHYL]-4-ETHYL-5-(METHOXYMETHYL)PYRIMIDINE

A solution of 4-ethyl-5-hydroxymethyl-2-methylthiopyrimidine (0.63 g, 3.42 mmol), Ag$_2$O (1.6 g, 6.9 mmol) and MeI (1.1 mL, 17.1 mmol) in CH$_3$CN (10 mL) was stirred overnight, filtered and concentrated to give 4-ethyl-5-methoxymethyl-2-methylthiopyrimidine in 98% yield (0.66 g); GC/MS calcd. for C$_9$H$_{14}$N$_2$OS (M+) 198, found 198. The title compound was then prepared by (a) oxidation of 4-ethyl-5-methoxymethyl-2-methylthiopyrimidine (0.66 g, 3.35 mmol) with mCPBA (1.18 g, 6.85 mmol) as described for Example 67, and (b) reaction with methyl hydrazine (0.36 mL, 6.85 mmol) followed by citraconic anhydride (0.77 g, 6.85 mmol) also described in Example 67; resulting in a yield of 41% (0.40 g) from 4-ethyl-5-methoxymethyl-2-methylthiopyrimidine; $^1$H NMR (CDCl$_3$) δ 8.14 (s, 1H), 6.43 (s, 1H), 4.29 (s, 2H), 3.53 (s, 3H), 3.36 (s, 3H), 2.68 (m, 2H), 2.14 (s, 3H), 1.13 (m, 3H).

Example 113

2-[N-(1'-AMINOCITRACONAMIDO)]-5-(METHOXYMETHYL)-4-TRIFLUOROMETHYLPYRIMIDINE

The title compound was prepared as described for Example 112, but employing of 4-trifluoromethyl-5-hydroxymethyl-2-methylthiopyrimidine (0.50 g, 2.23 mmol) (prepared in analogy to Example 110) where 4-ethyl-5-hydroxymethyl-2-methylthiopyrimidine was used, and employing hydrazine (0.09 mL, 2.87 mmol) where methyl hydrazine was used, resulting in an overall yield of 35% (0.25 g); $^1$H NMR (CDCl$_3$) δ 8.63 (s, 1H), 8.20 (s, 1H), 6.48 (s, 1H), 4.46 (s, 2H), 3.75 (s, 3H), 2.12 (s, 3H).

Example 114

2-[N-(1'-AMINOCITRACONAMIDO)]-5-(ETHOXYMETHYLCARBONATE)-4-TRIFLUOROMETHYLPYRIMIDINE

To a solution of 2-[N-(1'-aminocitraconamido)]-4-trifluoromethylpyrimidine-5-carboxylic acid (0.10 g, 0.317 mmol) and N-methylmorpholine (0.035 mL, 0.317 mmol) in THF (10 mL) at 0° C. was added ethylchloroformate (0.030 mL, 0.317 mmol). After stirring 5 minutes, NaBH$_4$ (0.040 g, 1.05 mmol) was added, MeOH (7 mL) was added, and the mixture was stirred 10 minutes then concentrated. The oil was dissolved in EtOAc (30 mL) and washed with 1N HCl (10 mL), 1N NaHCO$_3$ (10 mL), and brine (10 mL), dried (MgSO$_4$), concentrated and chromatographed (SiO$_2$, hexanes/EtOAc, 2:1) to provide the title compound in 19% yield (0.022 g); $^1$H NMR (CDCl$_3$) δ 9.03 (s, 1H), 6.53 (s, 1H), 4.88 (s, 2H), 4.36 (q, 2H), 2.19 (s, 3H), 1.32 (t, 3H).

Example 115

ETHYL 4-[N-(1'-AMINOCITRACONAMIDO)]-2-PHENYLPYRIDINE-5-CARBOXYLATE

The title compound was prepared by (a) reaction of diethylethoxymethylenemalonate (31 g, 144 mmol) with benzamidine (22 g, 144 mmol) under basic conditions to afford ethyl 2-phenyl-4-hydroxypyrimidine-5-carboxylate in 64% yield in analogy to Example 15, (b) reaction of ethyl 2-phenyl-4-hydroxypyrimidine-5-carboxylate (1.5 g, 6 mmol) and POCl$_3$ (9.4 g, 62 mmol) to afford 81% of ethyl 2-phenyl-4-chloropyrimidine-5-carboxylate in analogy to Example 7, (c) reaction of ethyl 2-phenyl-4-chloropyrimidine-5-carboxylate (12 g, 46 mmol) with hydrazine (4.4 g, 137 mmol) to afford 99% of ethyl 4-hydrazino-2-phenylpyrimidine-5-carboxylate in analogy to Example 18, (d) reaction of ethyl 4-hydrazino-2-phenylpyrimidine-5-carboxylate (12 g, 46 mmol) with citraconic anhydride (10 g, 92 mmol) to afford 75% (12 g) of the title compound (m.p. 155–156° C.) in analogy to Example 21.

Example 116

ETHYL-4-[N-(1'-AMINOCITRACONAMIDO)-N-METHYL]-2-PHENYLPYRIMIDINE-5-CARBOXYLATE

The title compound was prepared according to the procedure of Example 68 but employing ethyl 2-[N-(1'-aminocitraconamide)]-4-phenylpyrimidine-5-carboxylate (0.1 g, 0.3 mmol) and methyl iodide (0.09 g, 0.7 mmol) under basic conditions, resulting in a yield of 45% (0.05 g); m.p. 118–119° C.

Example 117

ETHYL 4-[N-ACETYL-N-(1'-AMINOCITRACONAMIDO)]-2-PHENYLPYRIMIDINE-5-CARBOXYLATE

The title compound was prepared according to the procedure of Example 75 but employing ethyl 2-[N-(1'-aminocitraconamide)]-4-phenylpyrimidine-5-carboxylate (0.5 g, 1.3 mmol, prepared in Example 115) and acetic anhydride (5 mL) under basic conditions, resulting in a yield of 10% (0.05 g); $^1$HNMR (CDCl$_3$) δ 9.15 (d, 1H), 8.19 (d, 2H), 7.47 (m, 3H), 6.70 (d, 1H), 4.42 (q, 2H), 2.28 (d, 6H), 1.43 (t, 3H).

Example 118

ETHYL 4-[N-(1'-AMINOCITRACONAMIDO)]-2-METHYLPYRIMIDINE-5-CARBOXYLATE

The title compound was prepared by (a) reaction of diethylethoxymethylenemalonate (6 g, 28 mmol) with acetamidine hydrochloride (3 g, 31 mmol) to afford 67% of ethyl 2-methyl-4-hydroxypyrimidine-5-carboxylate in analogy to Example 15, (b) reaction of ethyl 2-methyl-4-hydroxypyrimidine-5-carboxylate (2.8 g, 15 mmol) with POCl$_3$ (46 g, 300 mmol) to afford 28% of ethyl 4-chloro-2-methylpyrimidine-5-carboxylate, (c) reaction of ethyl 4-chloro-2-methylpyrimidine-5-carboxylate (0.25 g, 1.25 mmol) with hydrazine (0.2 g, 6.3 mmol) to afford 96% of 4-hydrazino-2-methylpyrimidine-5-carboxylate in analogy to Example 18, (d) reaction of 4-hydrazino-2-methylpyrimidine-5-carboxylate (0.24 g, 1.2 mmol) with citraconic anhydride (0.16 g, 1.44 mmol) to afford 70% (0.24 g) of the title compound (m.p. 98–99° C.) in analogy to Example 21.

Example 119

ETHYL 4-[N-(1'-AMINOCITRACONAMIDO)]-2-BENZYLPYRIMIDINE-5-CARBOXYLATE

The title compound was prepared by (a) reaction of diethyl ethoxymethylenemalonate (11 g, 52 mmol) with phenylacetamidine (8 g, 60 mmol) to afford 40% of ethyl 2-benzyl-4-hydroxypyrimidine-5-carboxylate in analogy to Example 15, (b) reaction of 2-benzyl-4-hydroxypyrimidine-5-carboxylate (3 g, 12 mmol) with POCl$_3$ (18 g, 116 mmol) to afford 45% of 2-benzyl-4-chloropyrimidine-5-carboxylate in analogy to Example 7, (c) reaction of 2-benzyl-4-chloropyrimidine-5-carboxylate (1.5 g, 5.5 mmol) with hydrazine (0.5 g, 16 mmol) to afford 75% of 2-benzyl-4-hydrazinopyrinmidine-5-carboxylate in analogy to Example 18, (d) reaction of ethyl 2-benzyl-4-hydrazinopyrimidine-5-carboxylate (1 g, 3.5 mmol) with citraconic anhydride (1 g, 11 mmol), in analogy to Example 21, to afford 70% (0.9 g) of the title compound; m.p. 117–118° C.

Example 120

ETHYL 4-[N-(1'-AMINOCITRACONAMIDO)]-2-(3'-NITROPHENYL)-PYRIMIDINE-5-CARBOXYLATE

The title compound was prepared by (a) reaction of diethyl ethoxymethylenemalonate (5 g, 24 mmol) with 3-nitrobenzamidine (5 g, 25 mmol) to afford 86% of ethyl 4-hydroxy-2-(3'-nitrophenyl)pyrimidine-5-carboxylate in analogy to Example 15, (b) reaction of ethyl 4-hydroxy-2-(3'-nitrophenyl)pyrimidine-5-carboxylate (6 g, 21 mmol) with (chloromethylene)dimethylammonium chloride (4 g, 31 mmol) concentration of reaction mixture, followed by hexane and ether wash afford 45% of ethyl 4-chloro-2-(3'-nitrophenyl)pyrimidine-5-carboxylate, (c) reaction of ethyl 4-chloro-2-(3'-nitrophenyl)pyrimidine-5-carboxylate (1.9 g, 6 mmol) with hydrazine (0.6 g, 18 mmol) to afford 33% of ethyl 4-hydrazino-2-(3'-nitrophenyl)pyrimidine-5- carboxylate in analogy to Example 18, (d) reaction of ethyl 4-hydrazino-2-(3'-nitrophenyl)pyrimidine-5-carboxylate (1.8 g, 6 mmol) with citraconic anhydride in analogy to Example 21, to afford 80% (0.5 g) of the title compound; m.p. 118–120° C.

Example 121

ETHYL 4-[N-(1'-AMINOCITRACONAMIDO)]-2-(4'-TRIFLUOROMETHYLPHENYL)PYRIMIDINE-5-CARBOXYLATE

The title compound was prepared by (a) of diethyl ethoxymethylenemalonate (6.3 g, 29 mmol) with 4-trifluoromethylphenylbenzamidine (5.5 g, 29 mmol) to afford 50% of ethyl 4-hydroxy-2-(4'-trifluoromethylphenyl) pyrimidine-5-carboxylate in analogy to Example 15, (b) reaction of ethyl 4-hydroxy-2-(4'-trifluoromethylphenyl) pyrimidine-5-carboxylate (3 g, 9.6 mmol) with $POCl_3$ (49 g, 322 mmol) to afford 97% of ethyl 4-chloro-2-(4'-trifluoromethylphenyl)pyrimidine-5-carboxylate in analogy to Example 7, (c) reaction of ethyl 4-chloro-2-(4'-trifluoromethylphenyl)pyrimidine-5-carboxylate (2 g, 6 mmol) with hydrazine (0.6 g, 18 mmol) to afford 60% of ethyl 4-hydrazino-2-(4'trifluoromethylphenyl)pyrimidine-5-carboxylate in analogy to Example 18, (d) reaction of ethyl 4-hydrazino-2-(4'-trifluoromethylphenyl)pyrimidine-5-carboxylate (1 g, 3 mmol) with citraconic anhydride (1 g, 9 mmol) to afford 40% (0.5 g) of the title compound (m.p. 148–150° C.) in analogy to Example 21.

Example 122

ETHYL 4-[N-(1'-AMINOCITRACONAMIDO)]-2-(2'-THIENYL)-PYRIMIDINE-5-CARBOXYLATE

The title compound was prepared by (a) reaction of diethyl ethoxymethylenemalonate (8 g, 35 mmol) with thienyl-2-formamidine hydrochloride (5.7 g, 35 mmol) to afford 74% of ethyl 4-hydroxy-2-(2'-thienyl)pyrimidine-5-carboxylate in analogy to Example 15, (b) reaction of ethyl 4-hydroxy-2-(2'-thienyl)pyrimidine-5-carboxylate (2 g, 8 mmol) with $POCl_3$ (24 g, 160 mmol) to afford 96% of ethyl 4-chloro-2-(2'-thienyl)pyrimidine-5-carboxylate in analogy to Example 7, (c) reaction of ethyl 4-chloro-2-(2'-thienyl pyrimidine-5-carboxylate (0.57 g, 2.2 mmol) with hydrazine (0.34 g, 11 mmol) to afford 99% of ethyl 4-hydrazino-2-(2'-thienyl)pyrimidine-5-carboxylate in analogy to Example 18, (d) reaction of ethyl 4-hydrazino-2-(2'-thienyl)pyrimidine-5-carboxylate (0.55 g, 2.1 mmol) with citraconic anhydride (0.71 g, 6.3 mmol) in analogy to Example 21 to afford 80% (0.61 g) of the title compound; m.p. 164–164° C.

Example 123

ETHYL 4-[N-(1'-AMINOCITRACONAMIDO)-N-METHYL]-2-(2'-THIENYL)-PYRIMIDINE-5-CARBOXYLATE

The title compound was prepared by (a) reaction of ethyl 4-chloro-2-(2'-thienylpyrimidine-5-carboxylate (0.3 g, 1.1 mmol)) with methylhydrazine (0.25 g, 5.6 mmol)) to afford 99% of ethyl 4-(1'-methylhydrazino)-2-(2'-thienyl) pyrimidine-5-carboxylate in analogy to Example 18, (b) reaction of ethyl 4-(1'-methylhydrazino)-2-(2'-thienyl) pyrimidine-5-carboxylate (0.3 g, 1 mmol)) with citraconic anhydride (0.4 g, 3 mmol) in analogy to Example 21 to afford 52% (0.21 g) of the title compound; m.p. 126–127° C.

Example 124

ETHYL 4-[N-(1'-AMINOCITRACONAMIDO)]-2-(3',4'-DICHLOROBENZYL)-PYRIMIDINE-5-CARBOXYLATE

The title compound was prepared by (a) of diethyl ethoxymethylenemalonate (6 g, 27 mmol) with 3',4'-dichlorophenylacetamidine (5.5 g, 27 mmol) to afford 37% of ethyl 4-hydroxy-2-(3',4'-dichlorobenzyl)pyrimidine-5-carboxylate in analogy to Example 15, (b) reaction of ethyl 4-hydroxy-2-(3',4'-dichlorobenzyl)pyrimidine-5-carboxylate (2 g, 6 mmol) with $POCl_3$ (14 g, 92 mmol) to afford 62% of ethyl 4-chloro-2-(3',4'-dichlorobenzyl) pyrimidine-5-carboxylate in analogy to Example 7, (c) reaction of ethyl 4-chloro-2-(3',4'-dichlorobenzyl)pyrimidine-5-carboxylate (1 g, 2.8 mmol) with hydrazine (0.27 g, 8.3 mmol) to afford 99% of ethyl 4-hydrazino-2-(3',4'-dichlorophenyl)pyrimidine-5-carboxylate in analogy to Example 18, (d) reaction of ethyl 4-hydrazino-2-(3',4'-dichlorobenzyl)pyrimidine-5-carboxylate (0.9 g, 2.7 mmol) with citraconic anhydride (0.49 g, 4.4 mmol) in analogy to Example 21 to afford 47% (0.3 g) of the title compound; m.p. 119–121° C.

Example 125

4-ETHYL-5-[2'-(4'-METHYL)OXAZOLYL]2-METHYLTHIOPYRIMIDINE

To a solution of 4-ethyl-2-methylthiopyrimidine-5-carboxylic acid (2.0 g, 10 mmol) in DMF (30 mL) was added $Na_2CO_3$ (2.1 g, 20 mmol) and chloroacetone (1.9 mL, 24 mmol). The reaction was stirred at 40° C. for 1 h., cooled to RT and ether (50 mL) was added. The solution was washed with $H_2O$ (3×20 mL), dried ($MgSO_4$), and concentrated. The residue was dissolved in xylene (100 mL), and acetamide (3.0 g, 50 mmol) and $BF_3(Et_2O)$ (0.7 mL) was added. The mixture was heated at 137° C. for 24 h., an additional aliquot of $BF_3(Et_2O)$ (1.4 mL) was added and the reaction was heated for an additional 24 h. The mixture was cooled to RT and concentrated. Chromatography ($SiO_2$, hexanes/EtOAc, 3:2) provided the title compound (0.25 g, 11% yield); m.p. 49–50° C.

Example 126

2-[N-(1'-AMINOCITRACONAMIDO)-N-METHYL]-4-ETHYL-5-[2"-(4"-METHYL)OXAZOLYL]PYRIMIDINE

The title compound was prepared by (a) oxidation of 4-ethyl-5-[2'-(4'-methyl)oxazolyl]-2-methylthiopyrimidine (0.25 g, 1.1 mol) with mCPBA (0.55 g, 3.2 mol) in analogy to Example 67, (b) reaction with methyl hydrazine (0.17 mL, 3.2 mol) in analogy to Example 104 (c) reaction with citraconic anhydride (0.29 mL, 3.2 mol) also in analogy to Example 104, to afford 6% (0.02 g) of the title compound; m.p. 85–86° C.

Example 127

2-[N-(1'-AMINOCITRACONAMIDO)-N-METHYL]-5-[2"-(4"-METHYL)OXAZOLYL]-4-(2'''-THIENYL)PYRIMIDINE

The title compound was prepared as described for Example 126, but employing 5-[2'-(4'-methyl)oxazolyl]-2-methylthio-4-(2"-thienyl)pyrimidine (0.19 g, 0.66 mmol) (prepared in analogy to Example 125), resulting in an overall yield of 12% (0.03 g); $^1$H NMR ($CDCl_3$) δ 8.50 (d, 1H), 7.40 (m, 2H), 7.01 (m, 2H), 6.50 (m, 1H), 3.61 (s, 3H), 2.21 (s, 3H), 1.58 (S, 3H).

Example 128

4-(BENZYLTHIO)-5-CYANO-2-(2'-THIENYL)PYRIMIDINE

A solution of ethyl 4-(benzylthio)-2-(2'-thienyl) pyrimidine-5-carboxylate (4 g; 11 mmol) and sodium hydroxide (0.9 g; 22 mmol) in 50% aqueous ethanol (244 mL) was stirred at room temperature for 23 h. The solution was concentrated and the residue was dissolved in water. The aqueous layer was acidified and the resulting solid was filtered to give 4-(benzylthio)-2-(2'-thienyl)-pyrimidine-5-carboxylic acid.

A solution of 4-(benzylthio)-2-(2'-thienyl)-pyrimidine-5-carboxylic acid (1.4 g, 4.3 mmol) in dichloromethane (22 mL) was stirred with oxalyl chloride (1.6 g, 13 mmol) and dimethyl formamide (4 drops) for 1 h. The mixture was concentrated and dried on a pump. The solid was dissolved in tetrahydrofuran (50 mL) and treated with a saturated solution of ammonia/tetrahydrofuran (100 mL). The solution was stirred for 1 h., concentrated and dried to give 4-(benzylthio)-2-(2'-thienyl)-pyrimidine-5-carboxamide (1.2 g, 85%). To this solid was added thionyl chloride (1.8 g; 15 mmol) and stirring continued for 1 h. The mixture was poured onto ice and extracted with ethyl acetate. The ethyl acetate layer was dried ($Na_2SO_4$), filtered and concentrated to give the title compound (0.94 g; 99%); 118–120° C.

Example 129

2-[N-(1'-AMINOCITRACONAMIDO)-N-METHYL]-4-ETHYL-5-[5"-METHYL-1",2",4"-OXADIAZOLYL]PYRIMIDINE

To a solution of 5-cyano-4-ethyl-2-methylthiopyrimidine (0.5 g, 2.8 mmol) (prepared in analogy to Example 128) in EtOH (50 mL) was added $K_2CO_3$ (1.9 g, 14 mmol) and hydroxylamine hydrochloride (0.97 g, 14 mmol). The reaction was refluxed overnight, filtered and concentrated. The residue was dissolved in pyridine (3 mL), acetyl chloride (0.4 mL, 5.6 mmol) was added, and the solution was refluxed for 1 hr. The mixture was allowed to cool to RT, $H_2O$ (5 mL) was added, and extracted with $CH_2Cl_2$ (2×25 mL). The organic solution was washed with brine (2×10 mL), dried ($MgSO_4$), and concentrated to give 4-ethyl-5-[5'-methyl-1',2',4'-oxadiazolyl]-2-methylthiopyrimidine in a 47% yield (0.31 g); GC/MS calcd for $C_{10}H_{12}N_4OS$ ($M^+$) 236, found 236.

The title compound was then prepared in analogy to Example 126, employing 4-ethyl-5-[5'-methyl-1',2',4'-oxadiazolyl]-2-methylthiopyrimidine (0.30 g, 1.3 mmol) in an overall yield of 10% (0.04 g); $^1$H NMR (CDCl3) δ 8.85 (d, 1H), 6.47 (s, 1H), 3.60 (s, 3H), 3.00 (m, 2H), 2.71 (s, 3H), 2.63 (s, 3H), 1.30 (m, 3H).

Example 130

ETHYL 4-(BENZYLTHIO)-2-(2'-THIENYL)PYRIMIDINE-5-CARBOXYLATE

A mixture of ethyl 4-chloro-2-(2'-thienyl)pyrimidine-5-carboxylate (12.6 g; 47 mmol), benzothiol (6.4 g; 52 mmol), potassium carbonate (7.2 g; 52 mmol) and tetrahydrofuran (235 mL) was heated at reflux for 48 h. The solution was filtered, concentrated and dried ($MgSO_4$) to give the title compound (16.4 g, 98% yield); m.p. 81–82° C.

Example 131

4-(BENZYLTHIO)-5-(3'-METHYLISOXAZOL-5'-YL)-2-(2"-THIENYL)PYRIMIDINE

A solution of n-butyllithium in hexane (4.6 mL; 7.3 mmol) was added under nitrogen to a solution of acetone oxime (0.27 g; 3.7 mmol) in tetrahydrofuran (7 mL) at 0° C. and stirred for 1 h. To this was added a solution of ethyl 4-(benzylthio)-2-(2'-thienyl)pyrimidine-5-carboxylate (1.0 g; 2.8 mmol) in tetrahydrofuran (5 mL) dropwise with stirring at 0° C. The solution was warmed to RT and stirred for 16 h. Concentrated sulfuric acid (1.6 g), tetrahydrofuran (7 mL) and water (2 mL) were added and the mixture was heated at reflux for 1 h. The solution was cooled to RT, made basic with potassium carbonate and extracted with methylene chloride. The organic layer was dried ($Na_2SO_4$), concentrated and chromatographed ($SiO_2$, 20% EtOAc in hexanes) to give the title compound (0.24 g; 23%); GC/MS calcd for $C_{19}H_{15}N_3OS_2$ ($M^+$) 365, found 365 ($M^+$).

Example 132

4-[N-(1'-AMINOCITRACONAMIDO)]-5-(3"-METHYLISOXAZOL-5'-YL)-2-(2'''-THIENYL)PYRIMIDINE

The title compound was prepared by (a) oxidation of 4-(benzylthio)-5-(3'-methylisoxazol-5'-yl)-2-(2"-thienyl)pyrimidine (0.23 g; 0.63 mmol) with mCPBA (0.55 g; 3.2 mmol) in dichloromethane (6.3 mL) in analogy to Example 67, (b) reaction with hydrazine (0.09 g; 3 mmol) in tetrahydrofuran (5.4 mL) in analogy to Example 18, (c) reaction with citraconic anhydride (0.17 g; 1.5 mmol) in chloroform (5 mL) in analogy to Example 20, to provide the title compound in an overall yield of 33% (0.076 g); m.p. 256–257° C.

Example 133

4-(BENZYLTHIO)-5-(TETRAZOLYL)-2-(2'-THIENYL)PYRIMIDINE

A mixture of 4-(benzylthio)-5-cyano-2-(2'-thienyl)pyrimidine (2.0 g, 6.5 mmol), sodium azide (0.55 g, 8.4 mmol), ammonium chloride (0.45 g, 8.4 mmol) and dimethyl formamide (20 mL) was heated at 100° C. for 24 h. The mixture was then concentrated to an oil, dissolved in ethyl acetate and washed with 1N hydrochloric acid. The organic layer was dried ($Na_2SO_4$), filtered and concentrated to give the title compound (1.0 g; 44%); m.p. 203–205° C.

Example 134

4-(BENZYLTHIO)-5-(N-METHYL TETRAZOLYL)-2-(2'-THIENYL)PYRIMIDINE

A mixture of 4-(benzylthio)-5-(tetrazolyl)-2-(2'-thienyl)pyrimidine (0.95 g, 2.7 mmol), iodomethane (1.9 g, 13 mmol), potassium carbonate (1.9 g, 13 mmol) and dimethyl formamide (20 mL) was heated at 50° C. for 20 h. The mixture was concentrated, dissolved in ethyl acetate and washed with water. The ethyl acetate layer was dried ($Na_2SO_4$), filtered and concentrated to give the title compound; m.p. 133–136° C.

Example 135

4-[N-(1'-AMINOCITRACONAMIDO)]-5-(N-METHYL TETRAZOLYL)-2-(2"-THIENYL)PYRIMIDINE

The title compound was prepared by (a) oxidation of 4-(benzylthio)-5-(N-methyl tetrazolyl)-2-(2'-thienyl)pyrimidine (1.0 g, 2.7 mmol) with mCPBA (1.2 g; 7.0 mmol) to provide 4-benzylsulfonyl-5-(N-methyl tetrazolyl)-2-(2'-thienyl)pyrimidine in analogy to Example 67, (b) reaction of 4-benzylsulfonyl-5-(N-methyl tetrazolyl)-2-(2'-thienyl)pyrimidine (0.45 g, 1.1 mmol) with hydrazine (0.11 g, 3.3 mmol) in chloroform (33 mL) to provide 4-hydrazino-5-(N-methyl tetrazolyl)-2-(2'-thienyl)pyrimidine in analogy to Example 18 (c) reaction of 4-hydrazino-5-(N-methyl tetrazolyl)-2-(2'-thienyl)pyrimidine with citraconic anhydride in analogy to Example 20 resulted in a yield of 24% (0.1 g); m.p. 201–202° C.

Example 136

4-(BENZYLTHIO)-5-(4'-METHYLOXAZOL-2-YL)-2-(2''-THIENYL)PYRIMIDINE

The title compound was prepared as described in Example 125, but employing 4-(benzylthio)-2-(2'-thienyl)pyrimidine-5-carboxylic acid (2 g, 6 mmol), chloroacetone (1.1 g, 12 mmol), sodium carbonate (1.3 g, 12 mmol) and dimethyl formamide (61 mL) followed by $BF_3/Et_2O$ (0.4 g, 3 mmol), acetamide (0.8 g, 13 mmol) and xylene (26 mL) to give the title compound in a yield of 9% (0.08 g); m.p. 169–170° C.

Example 137

4-[N-(1'-AMINOCITRACONAMIDO)]-5-(4''-METHYLOXAZOL-2-YL)-2-(2'''-THIENYL)PYRIMIDINE

The title compound was prepared according to the procedure of Example 135, but employing 4-(benzylthio)-5-(4'-methyloxazol-2-yl)-2-(2''-thienyl)pyrimidine (0.08 g, 0.23 mmol), mCPBA (0.2 g; 1.2 mmol) and chloroform (10 mL); followed by hydrazine and tetrahydrofuran in analogy to Example 18, and citraconic anhydride in chloroform in analogy to Example 20 to provide the title compound in an overall yield of 35% (0.03 g); m.p. 246–247° C.

Example 138

4-(BENZYLTHIO)-N-(2'-HYDROXYETHYL)-2-(2''-THIENYL)PYRIMIDINE-5-CARBOXAMIDE

A solution of 4-(benzylthio)-2-(2'-thienyl)pyrimidine-5-carboxylic acid (1.0 g, 3.1 mmol) in dichloromethane (31 mL) was stirred with oxalyl chloride (1.2 g, 9.2 mmol) and dimethyl formamide (4 drops) for 2 h. The mixture was concentrated and dissolved in tetrahydrofuran (61 mL). To this was added 2-aminoethanol (0.37 g, 6.1 mmol) and stirring continued for 2 h. at RT. The mixture was concentrated, dissolved in ethyl acetate, washed with water and dried ($Na_2SO_4$). The ethyl acetate layer was concentrated to give the title compound (1.2 g, 99%); m.p. 147–148° C.

Example 139

4-(BENZYLTHIO)-5-(4',5'-DIHYDRO-2'-OXAZOLYL)-2-(2''-THIENYL)PYRIMIDINE

To a mixture of 4-(benzylthio)-N-(2'-hydroxyethyl)-2-(2''-thienyl)pyrimidine-5-carboxamide (1.1 g, 3.0 mmol) in 50% ethyl acetate/chloroform (260 mL) was added thionyl chloride (0.57 g, 4.8 mmol). The mixture was heated at reflux for 5 h., cooled and filtered. The solid was washed with water and dried to give the title compound (0.7 g; 64%); m.p. 191–192° C.

Example 140

4-[N-(1'-AMINOCIACONAMIDO)]-5-(4'',5''-DIHYDRO-2''-OXAZOLYL)-2-(2'''-THIENYL)PYRIMIDINE

The title compound was prepared by (a) oxidation of 4-(benzylthio)-5-(4'',5''-dihydro-2''-oxazolyl)-2-(2'''-thienyl)pyrimidine (0.5 g, 1.4 mmol) with mCPBA (1.2 g; 7.1 mmol) in analogy to Example 67, (b) reaction with hydrazine (0.17 g, 5.2 mmol in analogy to Example 18 (c) reaction with citraconic anhydride (0.23 g; 2.0 mmol) in analogy to Example 20, resulting in the title compound in a yield of 36% (0.18 g); m.p. 258–259° C.

Example 141

4-(BENZYLTHIO)-5-(5'-METHYL-1',3',4'-OXADIAZOL-2'-YL)-2-(2''-THIENYL)PYRIMIDINE

A mixture of 4-(benzylthio)-2-(2'-thienyl)pyrimidine-5-carboxylic acid (1.0 g, 3.0 mmol), phosphorous oxychloride (2.96 mL) and N-acetylhydrazide (0.24 g, 3.3 mmol) was heated at reflux under nitrogen for 2 h. The mixture was poured onto ice, made basic with ammonium hydroxide and extracted with dichloromethane. The organic layer was dried ($Na_2SO_4$), filtered and concentrated to provide the title compound in a yield of 83% (0.9 g,); GC/MS, calcd for $C_{18}H_{14}N_4OS_2(M^+)$366, found 366.

Example 142

4-[N-(1'-AMINOCITRACONAMIDO)]-5-(5''-METHYL-1'',3'',4''-OXADIAZOL-2''-YL)-2-(2'''-THIENYL)PYRIMIDINE

The title compound was prepared by (a) oxidation of 4-(benzylthio)-5-(5'-methyl-1',3',4'-oxadiazol-2'-yl)-2-(2''-thienyl)pyrimidine (0.5 g, 1.4 mmol) with mCPBA (1.2 g; 7.1 mmol) in analogy to Example 67, (b) reaction of 4-(benzylsulfonyl)-5-(5'-methyl-1',3',4'-oxadiazol-2'-yl)-2-(2''-thienyl) pyrimidine (0.4 g, 1 mmol) and hydrazine (0.16 g, 5 mmol) in analogy to Example 18, (c) reaction of 4-hydrazino-5-(5'-methyl-1',3',4'-oxadiazol-2'-yl)-2-(2''-thienyl)pyrimidine (0.22 g, 0.8 mmol) and citraconic anhydride (0.2 g; 1.8 mmol) in analogy to Example 20 to provide the title compound in a yield of 37% (110 mg); m.p. 229–230° C.

Example 143

4-[N-(1'-AMINOCITRACONAMIDO)]-5-CYANO-2-(2'-THIENYL)PYRIMIDINE

The title compound was prepared by (a) oxidation of 4-(benzylthio)-5-cyano-2-(2'-thienyl)pyrimidine (0.5 g, 1.6 mmol) with mCPBA (1.4 g; 8.1 mmol) in analogy to Example 67, (b) reaction of 4-(benzylsulfonyl)-5-cyano-2-(2'-thienyl) pyrimidine (0.5 g, 1.5 mmol) with hydrazine (0.24 g, 7.4 mmol) in tetrahydrofuran in analogy to Example 104, (c) reaction of 5-cyano-4-hydrazino-2-(2'-thienyl) pyrimidine (0.3 g, 1.4 mmol) and citraconic anhydride (0.34 g; 3.0 mmol) in analogy to Example 20 to provide the title compound in a yield of 58% (0.25 g).

Example 144

SYNTHESIS OF REPRESENTATIVE COMPOUNDS BY COMBINATORIAL CHEMISTRY TECHNIQUES

This example illustrates the synthesis of a representative class of compounds of this invention, 2-substituted-4-trifluoromethyl-5-pyrimidine carboxylic acid methyl esters, by combinatorial chemistry. It should be understood that, while a specific class of compounds are illustrated in this example, the following procedure may be employed to synthesize other compounds of this invention.

A mixture of TentaGel resin (TentaGel S PHB, Advanced Chem Tec Louisville, Ky., 17 g, 0.2 mmol/g reactive sites) containing a free hydroxy as the reactive site and DMF (75 mL) was stored for 0.25 h. Then a solution of 2-chloro-4-trifluoromethyl pyrimidine-5-carbonyl chloride (2.20 g, 10.2 mmol) in DMF (15 mL) was added. The mixture was gently shaken for 3 h and filtered. The resin was washed thoroughly with DMF (3×100 mL) and $CH_2Cl_2$ (3×100 mL) and then dried under vacuum. The resin was divided into 80 equal portions and placed into 80 separate reaction vessels (dispersion tubes). The dispersion tubes were placed into separate test tubes each containing a different amine (2.5 mmol, Appendix I) and 2 mL of a 0.1M solution of pyridine/DMF (5 molar equivalents of each amine in each test tube). The entire set of 80 reaction vessels was gently shaken for 5 hours to ensure complete reaction. Then each of the dispersion tubes was removed from the test tube containing the amine and rinsed separately to remove any unreacted materials. The dispersion tubes were then dried and submersed into 80 new test tubes (previously tared), each containing a solution of NaOMe (2.5 mL, 0.012M solution, 0.03 mmol). The reaction was allowed to proceed overnight at room temperature under $N_2$. Then the dispersion tubes were removed from the solution and individually rinsed with MeOH. The individual MeOH solutions were concentrated in the tared test tubes to provide known amounts of the desired 80 individual methyl esters substituted with different groups at the 2-position. Each compound was >85% pure by HPLC and had the correct molecular weight as determined by GC/MS.

Example 145

INHIBITION OF THE ACTIVATION OF NFκB AND AP-1

A. NFκB ASSAY

Stable human Jurkat T-cells containing an NFκB binding site (from the MHC promoter) fused to a minimal SV-40 promoter driving luciferase expression were used in this experiment. Cells were split to $3\times10^5$ cells/mL every 2–3 days (cell concentration should not exceed $1\times10^6$ cells/mL to keep the cells proliferating in log phase). These cells were counted, resuspended in fresh medium containing 10% Serum-Plus at a density of $1\times10^6$ cells/mL and plated in 96 well round bottom plates (200 μA per well) 18 hours prior to starting the experiment.

Compounds of this invention, dissolved in dimethyl sulfoxide (3.3, 0.33 and 0.03 μg/mL), were then added to the 96 well plates containing the cells and the plates were incubated for 0.5 h at 37° C. Then 50 ng/mL of phorbol 12-myristate-13-acetate (PMA) and 1 μg/mL of phytohemagglutinin (PHA) were added to each well and the cells were incubated for an additional 5 h at 37° C. The plates were centrifuged at 2200 RPM for 3 minutes at room temperature and then the medium was removed. To each well was added 60 μL of cell lysis buffer and the plates were left at room temperature for 0.25 h. Then 40 μL of each cell extract was transferred to a black 96 well plate and 50 μL of luciferase substrate buffer was added. Luminescence was immediately measured using a Packard TopCount.

B. AP-1 ASSAY

For AP-1, the assay was run as described above for NFκB except stable Jurkat T-cells were used that contained a collagenase promoter driving luciferase expression. In addition, the concentration of PMA used was 5 ng/mL.

C. RESULTS

Figure 4:
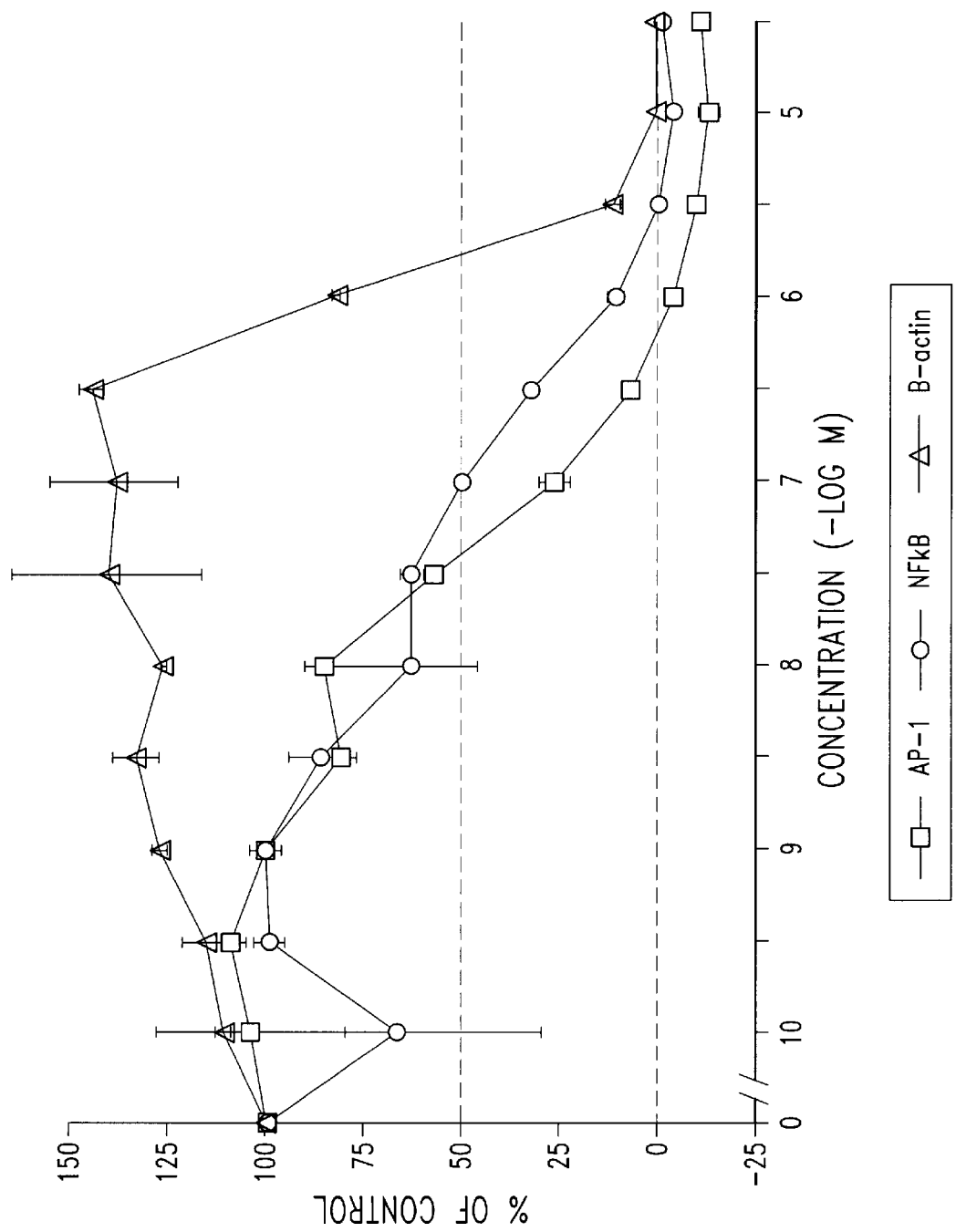
FIG. 4 illustrates the ability of a representative compound of this invention to inhibit the activation of NFκB and AP-1.

The results of the above assays for a representative compound of this invention, ethyl 2-[N-(1'-aminocitraconamido)]-4-pentafluoroethylpyrimidine-5-carboxylate (see Example 48), as percent inhibition versus control are presented in FIG. 4. This figure also indicates activity of β-actin which was employed in these assays as a control cell line indicating effects on transcription. The lack of β-actin activity evidences selectivity of the test compounds for the transcription factors AP-1 and NFκB.

Expressed as $IC_{50}$'s, the results of these assays on additional test compounds are summarized in Table 3 below. The $IC_{50}$ values reported in Table 3 are the average of the measurements obtained from the NFκB and AP-1 assays described above.

TABLE 3

Ability of Representative Compounds of Structure (I) to Inhibit NFκB and AP-1

| Test Compound (Example No.) | $IC_m$ (μM) |
| --- | --- |
| 20 | 0.7 |
| 21 | 0.5 |
| 23 | 5–10 |
| 36 | 0.15 |
| 37 | 0.15 |
| 38 | 0.04 |
| 40 | 1.0 |
| 41 | 3.9 |
| 42 | 5 |
| 44 | 10–30 |
| 46 | 4.0 |
| 48 | 0.09 |
| 50 | 1.0 |
| 52 | 2.0 |
| 64 | 1.0 |
| 68 | 0.4 |
| 73 | 0.05 |
| 74 | 0.45 |
| 75 | 0.4 |
| 77 | 1.3 |
| 78 | 0.15 |
| 79 | 0.2 |
| 81 | 0.1 |
| 83 | 0.08 |
| 84 | 0.45 |
| 85 | 0.02 |
| 87 | 0.55 |
| 88 | 0.5 |
| 89 | 0.2 |
| 90 | 0.06 |
| 91 | 1.1 |
| 92 | 0.3 |
| 93 | 0.8 |
| 94 | 1.1 |
| 95 | 0.3 |
| 96 | 0.7 |
| 97 | 0.9 |
| 98 | 6.0 |
| 99 | 0.4 |
| 100 | 0.8 |
| 101 | 0.6 |
| 102 | 0.4 |
| 103 | 0.4 |
| 104 | 0.2 |
| 105 | 2.4 |
| 106 | 1.7 |
| 107 | 0.5 |
| 108 | 1.5 |
| 109 | 0.2 |
| 111 | 4.9 |
| 112 | 0.6 |
| 113 | 1.0 |
| 114 | 1.1 |
| 115 | 0.03 |
| 116 | 1.4 |
| 117 | 4 |
| 118 | 17 |
| 119 | 7 |
| 120 | 8 |
| 121 | 0.4 |
| 122 | 0.02 |
| 123 | 0.8 |

TABLE 3-continued

Ability of Representative Compounds of Structure (I) to Inhibit $NF_\kappa B$ and AP-1

| Test Compound (Example No.) | $IC_m$ ($\mu M$) |
|---|---|
| 124 | 4 |
| 126 | 1.0 |
| 127 | 0.75 |
| 129 | 1.42 |
| 132 | 0.19 |
| 135 | 0.12 |
| 137 | 0.31 |
| 140 | 0.2 |
| 142 | 0.25 |
| 143 | 5.15 |

Based on the above results, representative compounds of this invention were found to be effective at inhibiting the activation of transcription factors (i.e., $NF\kappa B$ and AP-1) involved in gene transcription, and therefore have utility as, for example, immunosuppressive agents.

Example 146

INHIBITION OF CYTOKINES

Figure 5:
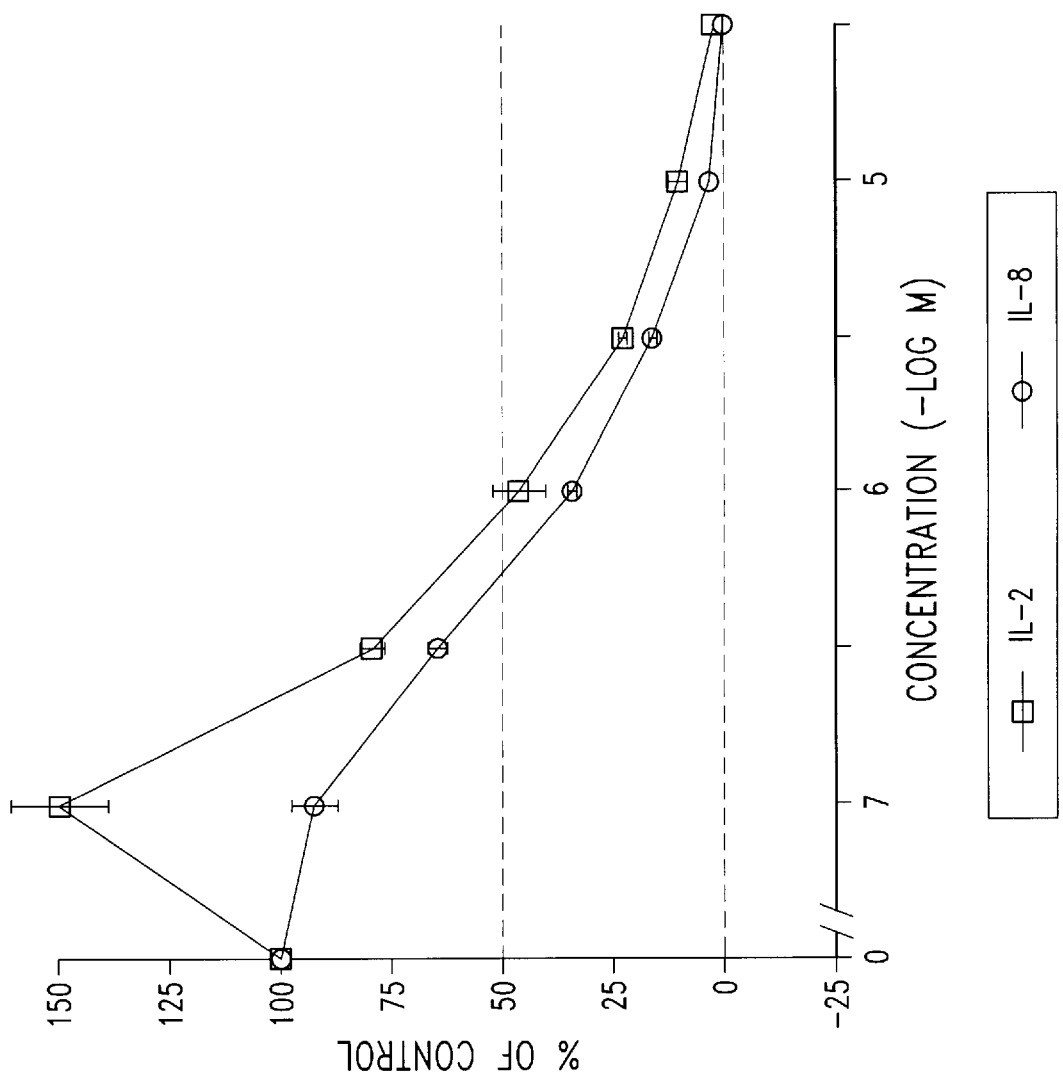
FIG. 5 illustrates the ability of a representative compound of this invention to inhibit IL-2 and IL-8.

To determine the effects of compounds on PMA/PHA-induced cytokine production, supernatants from either the $NF\kappa B$ (for IL-8) and AP-1 (for IL-2) reporter gene assays of Example 145 were collected and saved. Cytokine levels in the supernatants (25–50 $\mu L$ aliquots) were determined by ELISA. The results of this experiment for a representative compound of this invention, ethyl 2-[N-(1'-aminocitraconamido)]-4-pentafluoroethylpyrimidine-5-carboxylate (see Example 48), is presented in FIG. 5 (expressed as percent inhibition versus control).

Example 147

ACTIVITY OF REPRESENTATIVE COMPOUND IN GRAFT VS. HOST AND CONTACT SENSITIVITY MODELS

The murine popliteal lymph node (PLN) assay is a graft vs. host model that predicts activity of compounds in blocking human transplant rejection. The delayed-type hypersensitivity response to oxazolone is a standard contact sensitivity model. Both of these models are used routinely to evaluate compounds that are used clinically. For example, cyclosporin and cyclophosphamide are active in these models and are used clinically (Morris et al., *Transplantation Proceedings* 22(Suppl. 1):110–112, 1990).

A. POPLITEAL LYMPH NODE MODEL

Spleens are removed from donor BALB/c mice and splenocytes are isolated then irradiated (3,000 rads) to prevent donor cell proliferation. After washing and adjusting cell density, $2.5 \times 10^6$ cells are injected subcutaneously into the left hind footpad of C3H mice. On day 4, the mice are sacrificed and left popliteal lymph nodes (PLNs) weighed.

A representative compound of this invention is administered once daily by intraperitoneal injection beginning one day before footpad injection (day 0) through day 4. The compound is suspended, immediately prior to use, at a concentration of 5 mg/ml in 0.25% methyl cellulose (Sigma) using a glass-Teflon homogenizer. For doses of 10, 20 and 30 mg/kg, appropriate dilutions of the stock solution are made so that 0.1 mL/10 g body weight is administered by intraperitoneal injection.

B. DELAYED TYPE HYPERSENSITIVITY STUDY

On day 0, oxazolone (100 mL of a 3% solution) is applied to the shaved abdomen of mice. On day 7, a challenge application of oxazolone is applied (10 mL) around the right ear. A representative compound of this invention is administered from days-2 to 7 by intraperitoneal injection. The injectable solution is prepared immediately prior to use by suspending the compound in 0.25% methyl cellulose (Sigma) using a glass-Teflon homogenizer. For each dose, 0.1 mL/10 g body weight of the suspension is administered. The compound is prepared at the highest concentration for this study and appropriate dilutions of the stock solution are made so that 0.1 mL/10 g body weight is administered. Twenty four hours later, the difference in right vs. left ear thickness is measured.

It will be appreciated that, although specific embodiments of this invention have been described herein for purpose of illustration, various modifications may be made without departing from the spirit and scope of the invention.

We claim:

1. A compound having the structure:

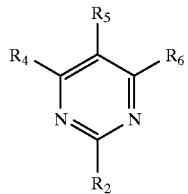

including pharmaceutically and prophylactically acceptable salts thereof, wherein $R_2$ is $R_{2a}$ when $R_4$ is $R_{4a}$, and $R_2$ is $R_{2b}$ when $R_4$ is $R_{4b}$;

$R_{2b}$ and $R_{4a}$ are selected from hydrogen, halogen and an unsubstituted or substituted $C_{1-8}$allyl, $C_{6-12}$aryl, $C_{7-12}$aralkyl, $C_{3-12}$heterocycle or $C_{4-16}$heterocyclealkyl;

$R_{2a}$ and $R_{4b}$ are selected from the following chemical moieties:

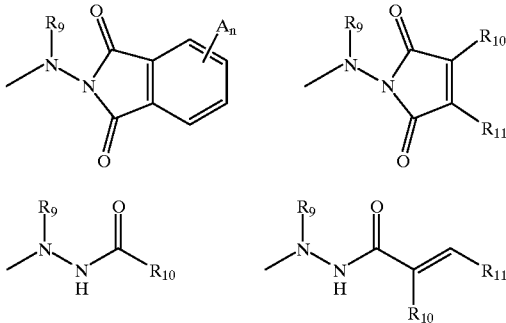

$R_5$ is selected from —C(=O)$OR_7$, —C(=O)$R_8$, —$CH_2O\{C(=O)O\}_{0,1}R_7$ and $R_{12}$;

$R_6$ is selected from hydrogen, —$CH_3$, —$CH_2C_6H_5$, —F and —$CF_3$;

$R_7$ is selected from hydrogen and a unsubstituted or substituted $C_{1-8}$alkyl, $C_{6-12}$aryl and $C_{7-12}$aralkyl;

$R_8$ is an unsubstituted or substituted $C_{1-8}$alkyl, $C_{6-12}$aryl or $C_{7-12}$aralkyl;

$R_9$ is selected from hydrogen —C(=O)—D—$R_7$ and an unsubstituted $C_{1-8}$alkyl or $C_{7-14}$aralkyl, wherein D is a direct bond, —O— or —NH—;

$R_{10}$ and $R_{11}$ are the same or different and independently selected from hydrogen and an unsubstituted or substituted $C_{1-8}$alkyl or $C_{6-12}$aryl;

$R_{12}$ is selected from cyano and the following chemical moieties:

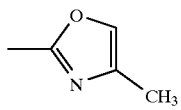 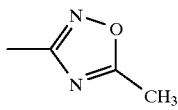

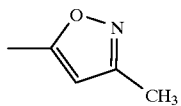 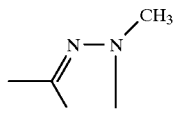

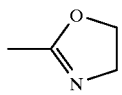 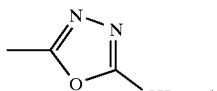

n is an integer from 0 to 4 and each occurrence of A is a substituent independently selected from halogen, —OH, —R, —OR, —COOH, —COOR, —COR, —CONH$_2$, —NH$_2$, —NHR, —NRR, NO$_2$, —SH, —SR, —SOOR, —SO$_3$R and —SOR, where each occurrence of R is independently selected from an unsubstituted or substituted C$_{1-8}$alkyl, C$_{6-12}$aryl or C$_{7-12}$aralkyl.

2. The compound of claim 1 wherein $R_2$ is $R_{2a}$, $R_4$ is $R_{4a}$, and $R_5$ is —C(=O)OR$_7$.

3. The compound of claim 2 wherein $R_{2a}$ is selected from one of the following structures:

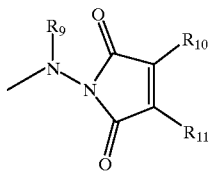 and 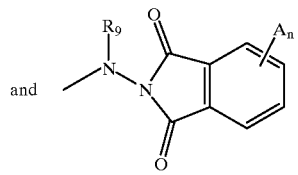

4. The compound of claim 2 wherein $R_{2a}$ is selected from one of the following structures:

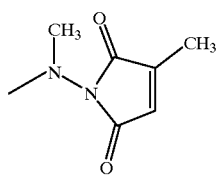 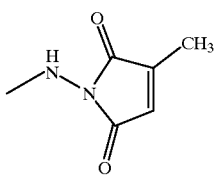

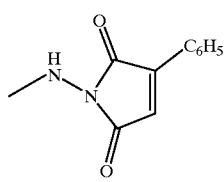 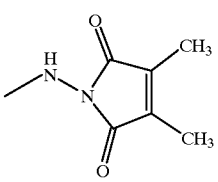

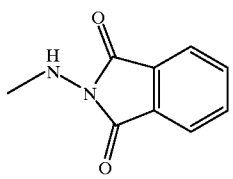

5. The compound of claim 2 wherein $R_{4a}$ is selected from —Cl, —CF$_3$, —CH$_3$, —(CH$_2$)$_{1-2}$CH$_3$, —C$_2$F$_3$,

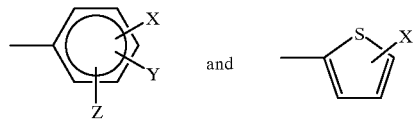 and 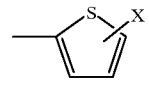

wherein X, Y and Z are the same or different, and independently selected from hydrogen, —OH, —R, —OR, —COOH, —COOR, —COR —CONH$_2$, —NH2, —NHR, —NRR, —NO$_2$, —SH, —SR, —SOOR, —SO$_3$R and —SOR, where each occurrence of R is independently selected from an unsubstituted or substituted C$_{1-8}$alkyl, C$_{6-12}$aryl, C$_{7-12}$aralkyl, C$_{3-12}$heterocycle or C$_{4-16}$heterocyclealkyl.

6. The compound of claim 2 wherein $R_6$ is selected from hydrogen, —CF$_3$ and —CH$_3$.

7. The compound of claim 2 wherein $R_7$ is selected from hydrogen, —CH$_3$ and —CH$_2$CH$_3$.

8. The compound of claim 2 wherein $R_9$ is selected from hydrogen, —CH$_3$, —CH$_2$CH$_3$ and —CH$_2$C$_6$H$_5$.

9. The compound of claim 2 wherein $R_{10}$ and $R_{11}$ are independently selected from hydrogen, —CH$_3$, —CF$_3$, —(CH$_2$)$_{1-5}$CH$_3$, —C$_6$H$_5$ and —CH$_2$C$_6$H$_5$.

10. The compound of claim 1 wherein $R_2$ is $R_{2b}$, $R_4$ is $R_{4b}$, and $R_5$ is —C(=O)OR$_7$.

11. The compound of claim 10 wherein $R_{4b}$ is selected from one of the following structures:

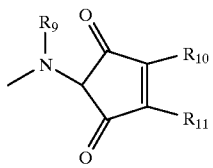 and 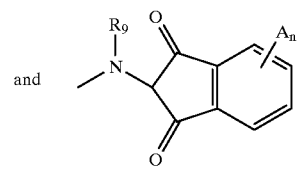

12. The compound of claim 10 wherein $R_{4b}$ is selected from one of the following structures:

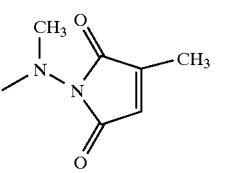 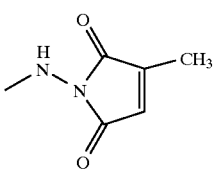

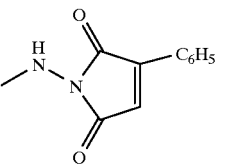 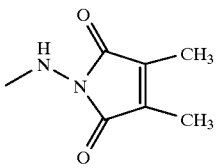

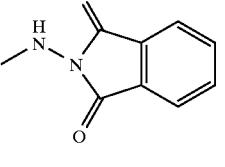

13. The compound of claim 10 wherein $R_{2b}$ is selected from —Cl, —CF$_3$, —CH$_3$, —C$_6$H$_5$, —(CH$_2$)$_{1-2}$CH$_3$, —C$_2$F$_3$,

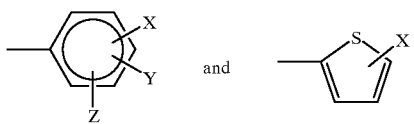 and 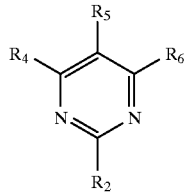

wherein X, Y and Z are the same or different, and independently selected from hydrogen, —OH, —R, —OR, —COOH, —COOR, —COR, —CONH$_2$, —NH$_2$, —NHR, —NRR, —NO$_2$, —SH, —SR, —SOOR, —SO$_3$R and —SOR, where each occurrence of R is independently selected from an unsubstituted or substituted C$_{1-8}$aklyl, C$_{6-12}$aryl, C$_{7-12}$aralkyl, C$_{3-12}$heterocycle or C$_{4-16}$heterocyclealkyl.

14. The compound of claim 10 wherein R$_6$ is selected from hydrogen, —CF$_3$ and —CH$_3$.

15. The compound of claim 10 wherein R$_7$ is selected from hydrogen, —CH$_3$ and —CH$_2$CH$_3$.

16. The compound of claim 10 wherein R$_9$ is selected from hydrogen, —CH$_3$, —CH$_2$CH$_3$ and —CH$_2$C$_6$H$_5$.

17. The compound of claim 10 wherein R$_{10}$ and R$_{11}$ are independently selected from hydrogen, —CH$_3$, —CF$_3$, —(CH$_2$)$_{1-5}$CH$_3$, —C$_6$H$_5$ and —CH$_2$C$_6$H$_5$.

18. The compound of claim 1 wherein the compound is selected from ethyl 2-(N-(1'-aminocitraconamido))-4-trifluoromethylpyrimidine-5-carboxylate; ethyl 2-(N-(1'-aminophthalimide))-4-trifluoromethylpyrimidine-5-carboxylate; 5-acetyl-2-(N-(1'-aminocitraconamido))-4-trifluoromethylpyrimidine-5-carboxylate; ethyl 2-(N-(1'-amino-3'-phenylmaleimido))-4-trifluoromethylpyrimidine-5-carboxylate; ethyl 2-(N-(1'-amino-3',4'-dimethylmaleimido))-4-trifluoromethylpyrimidine-5-carboxylate; ethyl 2-(N-(1'-aminocitraconamido)-N-methyl)-4-trifluoromethylpyrimidine-5-carboxylate; ethyl 4-(N-(1'-amino-3'-phenylmaleimido))-2-trifluoromethylpyrimidine-5-carboxylate; 4'-dimethylmaleimido))-2-trifluoromethylpyrimidine-5-carboxylate; ethyl 4-(N-(1'-amino-3',4'-dimethylmaleimido))-2-trifluoromethylpyrimidine-5-carboxylate; ethyl 2-(N-(1'-aminocitraconamido))-4-methylpyrimidine-5-carboxylate; ethyl 2-(N-(1'-aminocitraconamido))-4-pentafluoroethylpyrimidine-5-carboxylate; ethyl 2-(N-(1'-aminocitraconamido))-4-phenylpyrimidine-5-carboxylate; methyl 2-(N-(1'-aminocitraconamido))-4-(3'-pyridyl)pyrimidine-5-carboxylate; diethyl 2-(N-(1'-aminocitraconamido)) pyrimidine-4,5-dicarboxylate; ethyl 2-(N-(1'-aminocitraconamido))-4-(2'-thienyl)pyrimidine-5-carboxylate; ethyl 2-(N-(1'-aminocitraconamido)-N-methyl)-4-ethylpyrimidine-5-carboxylate; methyl 2-(N-(1'-aminocitraconamido))-4-(2'-thienyl)pyrimidine-5-carboxylate; ethyl 2-(N-(1'-aminocitraconamido)-N-methyl)-4-(2'-thienyl)pyrimidine-5-carboxylate; ethyl 2-(N-(1'-aminocitraconamido))-4-(5'-methyl-2'-thienyl) pyrimidine-5-carboxylate; ethyl 4-(N-(1'-aminocitraconamido))-2-phenylpyrimidine-5-carboxylate; and ethyl 4-(N-(1'-aminocitraconamido))-2-(2'-thienyl) pyrimidine-5-carboxylate.

19. A composition comprising a compound of claim 1 and a pharmaceutically or prophylactically acceptable carrier or diluent.

20. A method for treating an inflammatory condition comprising administering to a warm blooded animal in need thereof an effective amount of a compound of claim 1.

21. The method of claim 20 wherein the inflammatory condition is an immunoinflammatory condition.

22. The method of claim 20 wherein the inflammatory condition is an autoimmune disease.

23. A compound having the structure:

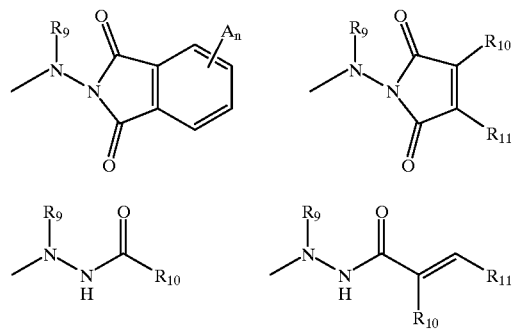

including pharmaceutically and prophylactically acceptable salts thereof, wherein R$_2$ is R$_{2a}$ when R$_4$ is R$_{4a}$, and R$_2$ is R$_{2b}$ when R$_4$ is R$_{4b}$;

R$_{2b}$ and R$_{4a}$ are selected from hydrogen, halogen and an unsubstituted or substituted C$_{1-8}$alkyl, C$_{6-12}$aryl, C$_{7-12}$aralkyl, C$_{3-12}$heterocycle or C$_{1-16}$heterocyclealkyl;

R$_{2a}$ and R$_{4b}$ are selected from the following chemical moieties:

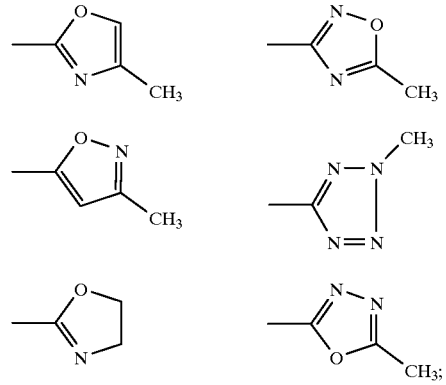

R$_5$ is selected from cyano and the following chemical moieties:

R$_6$ is selected from hydrogen, —CH$_3$, —CH$_2$C$_6$H$_5$, —F and —CF$_3$;

R$_7$ is selected from hydrogen and a unsubstituted or substituted C$_{1-8}$alkyl, C$_{6-12}$aryl and C$_{7-12}$aralkyl;

R$_8$ is an unsubstituted or substituted C$_{1-8}$alkyl, C$_{6-2}$aryl or C$_{7-12}$aralkyl;

R$_9$ is selected from hydrogen —C(=O)—D—R$_7$ and an unsubstituted C$_{1-8}$alkyl or C$_{7-14}$aralkyl, wherein D is a direct bond, —O— or —NH—;

R$_{10}$ and R$_{11}$ are the same or different and independently selected from hydrogen and an unsubstituted or substituted C$_{1-8}$alkyl or C$_{6-12}$aryl;

$R_{12}$ is selected from cyano and the following chemical moieties:

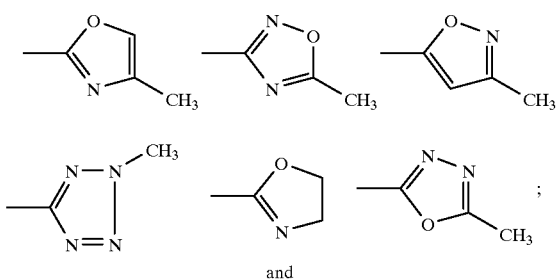

and n is an integer from 0 to 4 and each occurrence of A is a substituent independently selected from halogen, —OH, —R, —OR, —COOH, —COOR, —COR, —CONH$_2$, —NH$_2$, —NHR —NRR, NO$_2$, —SH, —SR, —SOOR, —SO$_3$R and —SOR, where each occurrence of R is independently selected from an unsubstituted or substituted $C_{1-8}$alkyl, $C_{6-12}$aryl or $C_{7-12}$aralkyl.

24. The compound of claim 23 wherein the compound is selected from 2-[N-(1'-aminocitraconamido)-N-methyl]-4-ethyl-5-[2"-(4"-methyl)oxazolyl]pyrimidine; 2-[N(1'-aminocitraconamido)-N-methyl]-5-[2"-(4"-methyl)oxazolyl]-4-(2'"-thienyl)pyrimidine; 2-[N-(1'-aminocitraconamido)-N-methyl]-4-ethyl-5-[5"-methyl-1", 2",4"-oxadiazolyl]pyrimidine; 4-[N-(1'-aminocitraconamido)]-5-(3"-methylisoxazol-5'-yl)-2-(2'"-thienyl)pyrimidine; 4-[N(1'-aminocitraconamido)]-5-(N-methyl tetrazolyl)-2-(2"-thienyl) pyrimidine; 4-[N(1'-aminocitraconamido)]-5-(4"-methyloxazol-2-yl)-2-(2'"-thienyl) pyrimidine; 4-[N-(1'-aminocitraconamido)]-5-(4", 5"-dihydro-2"-oxazolyl)-2-(2'"-thienyl)pyrimidine; 4-[N-(1'-aminocitraconamido)]-5-(5"-methyl-1",3",4"-oxadiazol-2"-yl)-2-(2'"-thienyl)pyrimidine; and 4-[N-(1'-aminocitraconamido)]-5-cyano-2-(2"-thienyl)pyrimidine.

* * * * *